(12) United States Patent
Foster et al.

(10) Patent No.: US 9,962,702 B2
(45) Date of Patent: *May 8, 2018

(54) PARTICLE MANIPULATION SYSTEM WITH OUT-OF-PLANE CHANNEL AND VARIABLE CROSS SECTION FOCUSING ELEMENT

(71) Applicant: Owl biomedical, Inc., Goleta, CA (US)

(72) Inventors: John S. Foster, Santa Barbara, CA (US); Kevin Shields, Santa Barbara, CA (US); Mehran Hoonejani, Goleta, CA (US)

(73) Assignee: Owl biomedical, Inc., Goleta, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/638,320

(22) Filed: Jun. 29, 2017

(65) Prior Publication Data
US 2017/0297025 A1 Oct. 19, 2017

Related U.S. Application Data

(63) Continuation-in-part of application No. 15/159,942, filed on May 20, 2016, which is a continuation of (Continued)

(51) Int. Cl.
*B01L 3/00* (2006.01)
*F16K 99/00* (2006.01)
(Continued)

(52) U.S. Cl.
CPC ... *B01L 3/502761* (2013.01); *B01L 3/502707* (2013.01); *B01L 3/502715* (2013.01);
(Continued)

(58) Field of Classification Search
CPC ..... B01L 2200/0652; B01L 2300/0627; B01L 2300/0654; B01L 2300/0864; B01L 2400/0622; B01L 2400/0633; B01L 3/502707; B01L 3/502715; B01L 3/502738; B01L 3/502761; F16K 99/0046;
(Continued)

(56) References Cited

U.S. PATENT DOCUMENTS

2012/0190104 A1   7/2012  Foster et al.

FOREIGN PATENT DOCUMENTS

WO    WO 2006/076567    7/2006

OTHER PUBLICATIONS

Xiaole Mao, et al. "Single-layer planar on-chip flow cytometer using microfluidic drifting based three-dimensional (3D) hydrodynamic focusing," Lab On a Chip, vol. 9, No. 11, Jan. 1, 2009, p. 1583.

*Primary Examiner* — Samuel P Siefke
(74) *Attorney, Agent, or Firm* — Jaquelin K. Spong

(57) ABSTRACT

A particle manipulation system uses a MEMS-based, microfabricated particle manipulation device which has a sample inlet channel, output channels, and a movable member formed on a substrate. The device may be used to separate a target particle from non-target material in a sample stream. In order to improve the sorter speed, accuracy or yield, the particle manipulation system may also include a microfluidic structure which focuses the target particles in a particular portion of the sample inlet channel. This focusing element may include cavities of variable cross section along the channel length. In addition, a filtering element may also be included upstream of the focusing element.

22 Claims, 19 Drawing Sheets

Related U.S. Application Data application No. 13/998,095, filed on Oct. 1, 2013, now Pat. No. 9,372,144.

(51) Int. Cl.
*G01N 21/64* (2006.01)
*G01N 15/14* (2006.01)

(52) U.S. Cl.
CPC .... *B01L 3/502738* (2013.01); *F16K 99/0046* (2013.01); *G01N 15/1404* (2013.01); *G01N 15/1484* (2013.01); *G01N 21/6402* (2013.01); *G01N 21/6428* (2013.01); *G01N 21/6486* (2013.01); *B01L 2200/0652* (2013.01); *B01L 2300/0627* (2013.01); *B01L 2300/0654* (2013.01); *B01L 2300/0864* (2013.01); *B01L 2400/0622* (2013.01); *B01L 2400/0633* (2013.01); *G01N 2015/149* (2013.01); *G01N 2021/6439* (2013.01); *G01N 2201/06113* (2013.01)

(58) Field of Classification Search
CPC ......... F16K 2099/0084; F16K 99/0011; F16K 99/0013; F16K 99/0028; G01N 15/1404; G01N 15/1484; G01N 2015/149; G01N 2021/6439; G01N 21/6402; G01N 21/6428; G01N 21/6486; G01N 2201/06113

See application file for complete search history.

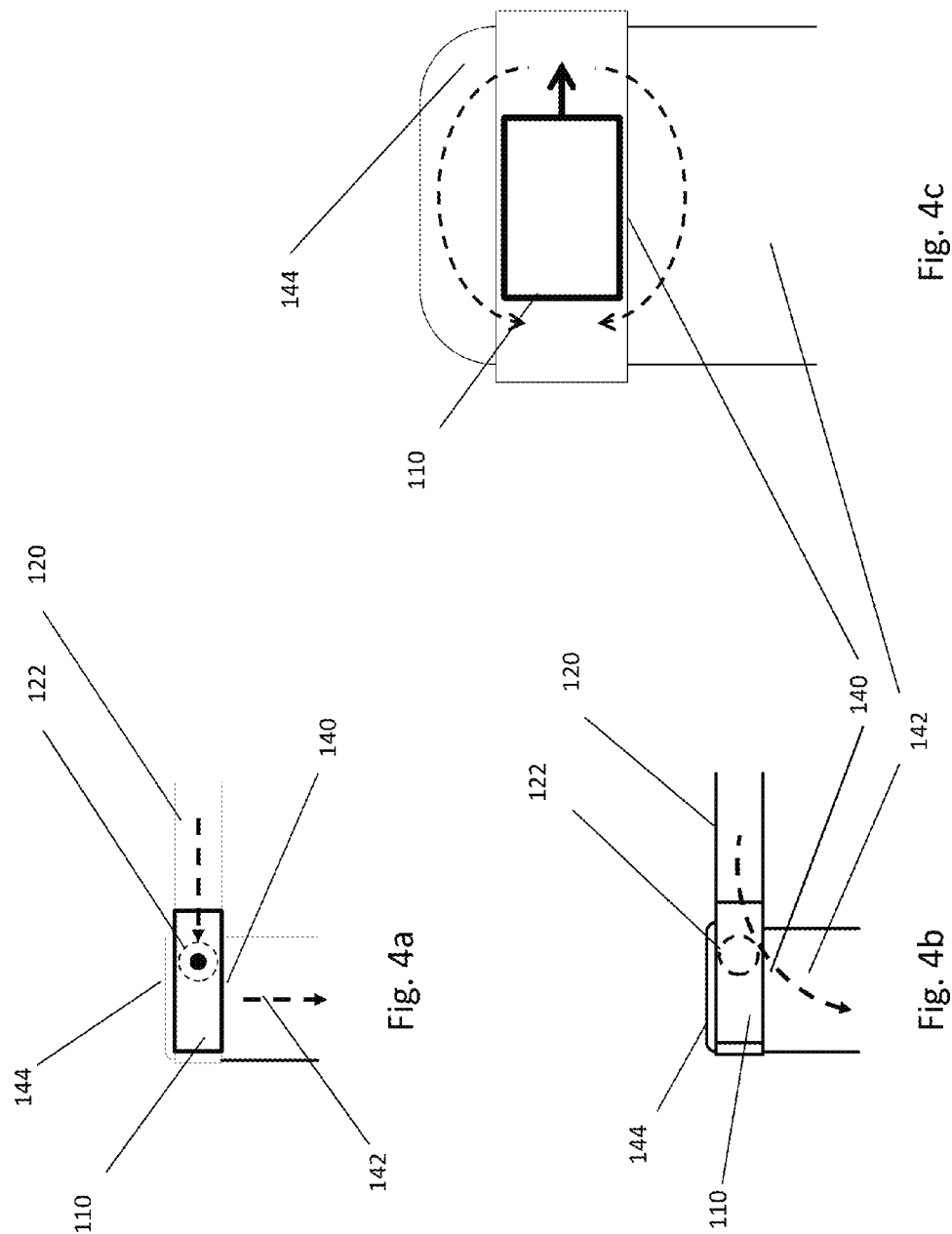

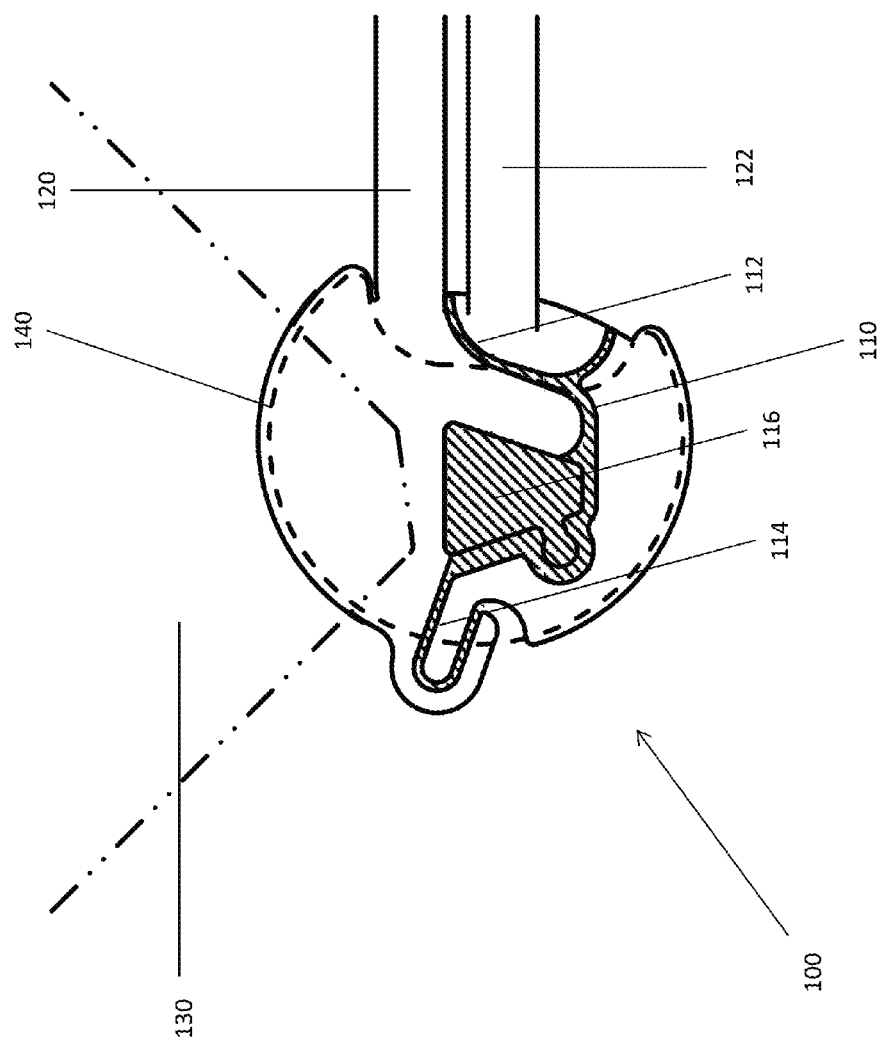

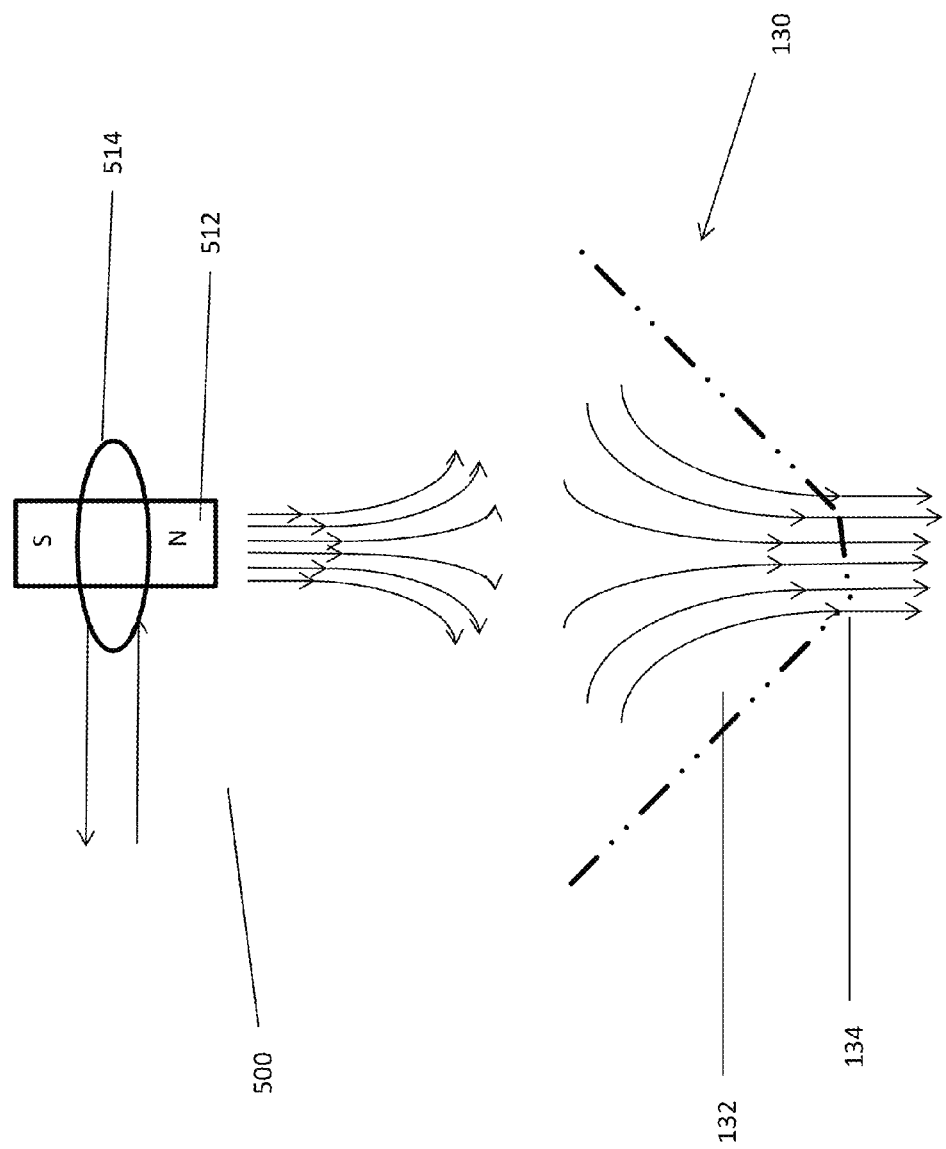

PARTICLE MANIPULATION SYSTEM WITH OUT-OF-PLANE CHANNEL AND VARIABLE CROSS SECTION FOCUSING ELEMENT

CROSS REFERENCE TO RELATED APPLICATIONS

This US Patent Application is a continuation in part from U.S. patent application Ser. No. 15/159,942, filed May 20, 2016, which is a continuation of U.S. patent application Ser. No. 13/998,096, filed. Oct. 1, 2013, now U.S. Pat. No. 9,404,838, each of which is incorporated by reference in its entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particles passing by the MEMS device in a fluid stream.

In another example, a MEMS devices may be a movable valve, used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to re-sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Additionally, U.S. patent application Ser. No. 13/374,899 (the '899 application) and Ser. No. 13/374,898 (the '898 application) provide further details of other MEMS designs. Each of these patents ('056, '972, '594 and '838) and patent applications ('898 and '899) is hereby incorporated by reference.

SUMMARY

One feature of the MEMS-based microfabricated particle sorting system is that the fluid may be confined to small, microfabricated channels formed in a semiconductor substrate throughout the sorting process. The MEMS device may be a valve which separates one or more target particles from other components of a sample stream. The MEMS device may redirect the particle flow from one channel into another channel, when a signal indicates that a target particle is present. This signal may be photons from a fluorescent tag which is affixed to the target particles and excited by laser illumination in an interrogation region upstream of the MEMS device. Thus, the MEMS device may be a particle or cell sorter operating on a fluid sample confined to a microfabricated fluidic channel, but using detection means similar to a FACS flow cytometer. In particular, the '898 application discloses a microfabricated fluidic valve wherein the sample inlet channel, sort channel and waste channel all flow in a plane parallel to the fabrication plane of the microfabricated fluidic valve.

A substantial improvement may be made over the prior art devices by having at least one of the microfabricated fluidic channels route the flow out of the plane of fabrication of the microfabricated valve. A valve with such an architecture has the advantage that the pressure resisting the valve movement is minimized when the valve opens or closes, because the movable member is not required to move a column of fluid out of the way. Instead, the fluid containing the non-target particles may move over and under the movable member to reach the waste channel. Furthermore, the force-generating apparatus may be disposed closer to the movable valve, resulting in higher forces and faster actuation speeds. As a result, the time required to open or close the valve may be much shorter than the prior art valve, improving sorting speed and accuracy. The systems and methods disclosed here may describe such a microfabricated particle sorting device with at least one out-of-plane channel. Furthermore, because of the small size of the features used in such a device, a fluidic focusing mechanism can dramatically improve the performance of the device by urging the particles into a portion of the fluidic channel. By locating the particles, the uncertainty is diminished, which may improve the sort speed and accuracy.

Accordingly, in the systems and methods disclosed here, a micromechanical particle manipulation device may be formed on a surface of a fabrication substrate. The micromechanical particle manipulation device may include a microfabricated, movable member formed on the substrate, and having a first diverting surface, wherein the movable member moves from a first position to a second position in response to a force applied to the movable member, wherein the motion is substantially in a plane parallel to the surface of the substrate. A sample inlet channel may be formed in the substrate and through which a fluid flows, the fluid including target particles and non-target material, wherein the flow in the sample inlet channel is substantially parallel to the surface, a plurality of output channels including a sort output channel into which the microfabricated member diverts the target particles, and a waste output channel into which the non-target material flows, and wherein the flow in waste output channel is substantially orthogonal to the plane, and wherein the waste output channel is located directly below at least a portion of the microfabricated member over at least a portion of its motion.

The system may further comprise a sheath fluid inlet in fluid communication with the sample inlet channel; and a focusing element coupled to the sheath fluid inlet, which is configured to urge the target particles into a particular portion of the sample inlet channel, wherein the focusing element comprises a microfabricated fluid channel with one substantially straight sidewall segment and an adjacent curved sidewall segment, wherein the straight and the curved sidewall segments define a fluid channel segment with a variable channel width. These variable channel width segments may define expansion/contraction cavities within the microfluidic channel, wherein the cavity is defined by the expanding portion followed by the contracting portion.

The particles suspended in the fluid stream may experience hydrodynamic forces as a result of these cavities. The first may be an inertial lift force, which is a combination of shear gradient lift resulting from the flow profile parabolic nature, and wall lift force. In addition, the particles may experience Dean flow drag: which is the drag force exerted on the particles as a result of the secondary dean flow induced by curved streamlines within the cavities. It is possible to balance these two forces by proper selection of the geometrical parameters of height, size, aspect ratio and placement with respect to the expansion/contraction cavities. Accordingly, these two forces may be balanced by introduction of the expansion-contraction cavities described below. This balance has not been achieved heretofore, but it may be achieved using the geometrical ranges set forth here.

These and other features and advantages are described in, or are apparent from, the following detailed description.

BRIEF DESCRIPTION OF THE DRAWINGS

Various exemplary details are described with reference to the following figures, wherein:

FIG. 4a is a simplified cross sectional view of a microfabricated particle sorting system in the actuated (sort) position, showing the flow of the sample stream into the sort channel which is in the same plane as the sample inlet channel; FIG. 4b is a simplified cross sectional view of a microfabricated particle sorting system in the quiescent (no sort) position, showing the flow of the sample stream into the waste channel which is not in the same plane as the sample inlet channel; FIG. 4c is a simplified cross sectional view of a microfabricated particle sorting system in the quiescent (no sort) position, showing the flow of the sample stream into the waste channel which is not in the same plane as the sample inlet channel, wherein the sample stream flows around the top and the bottom of the diverter;

FIG. 5 is a simplified plan view of a microfabricated particle sorting system in the quiescent (no sort) position, showing the stationary magnetically permeable feature;

FIG. 6 is a plan view of the actuation mechanism for the microfabricated particle sorting system, showing the functioning of the external magnetic field in combination with the stationary magnetically permeable feature;

It should be understood that the drawings are not necessarily to scale, and that like numbers may refer to like features.

DETAILED DESCRIPTION

The system described herein is a particle sorting system which may make use of the microchannel architecture of a MEMS particle manipulation system. More generally, the systems and methods describe a particle manipulation system with a sample inlet channel and a plurality of output channels, wherein at least one of the plurality of output channels is disposed in a different plane than the sample inlet channel. In addition, these microfluidic devices are made with very tight tolerances and narrow separations, which can benefit significantly from focusing the suspended particles into a smaller portion of the flow channel. As will be made clear in the discussion below, this architecture has some significant advantages relative to the prior art.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. In particular, it should be understood that the designations "sort" and "waste" are interchangeable, as they only refer to different populations of particles, and which population is called the "target" or "sort" population is arbitrary.

Figure 1:
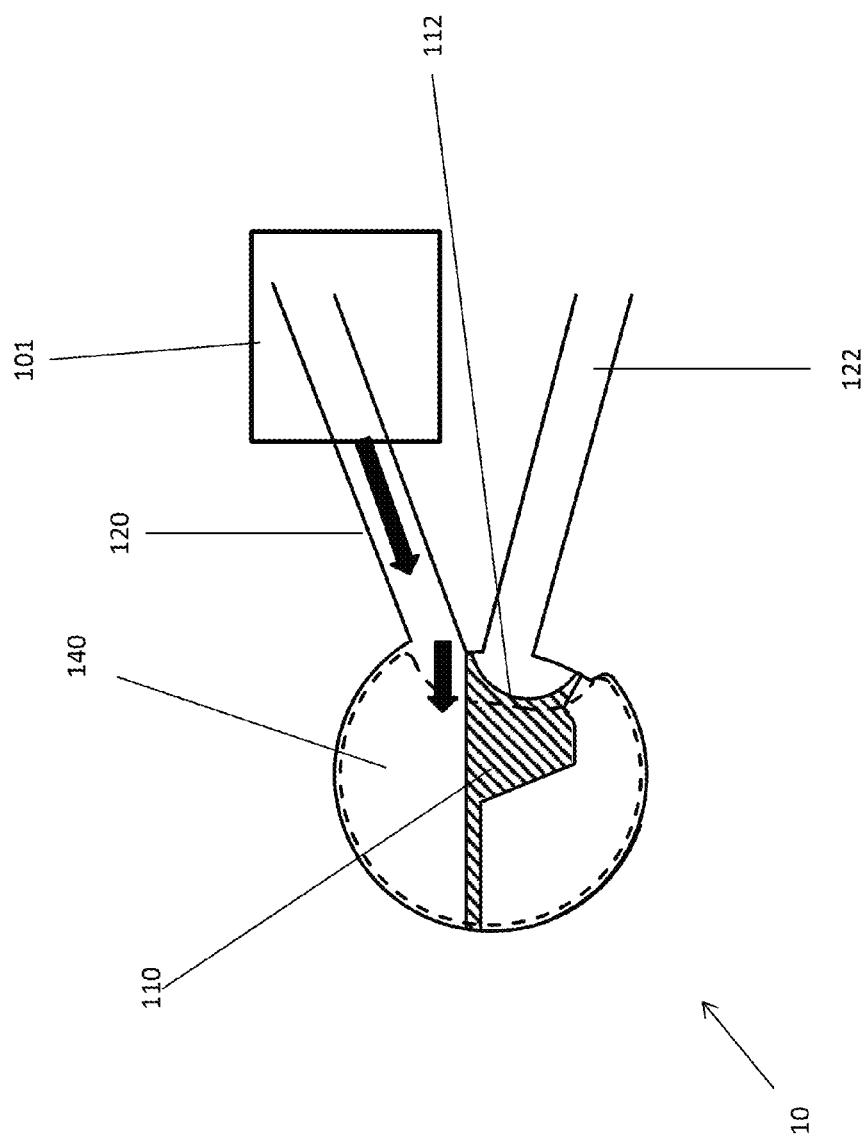
FIG. 1 is a simplified plan view of a microfabricated particle sorting system in the quiescent (no sort) position.

FIG. 1 is a plan view illustration of the novel microfabricated fluidic device 10 in the quiescent (un-actuated) position. The device 10 may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves.

A sample stream may be introduced to the microfabricated fluidic valve 110 by a sample inlet channel 120. The sample stream may contain a mixture of particles, including at least one desired, target particle and a number of other undesired, nontarget materials. The particles may be suspended in a fluid. For example, the target particle may be a biological material such as a stem cell, a cancer cell, a zygote, a protein, a T-cell, a bacteria, a component of blood, a DNA fragment, for example, suspended in a buffer fluid such as saline. The sample inlet channel 120 may be formed in the same fabrication plane as the valve 110, such that the flow of the fluid is substantially in that plane. The motion of the valve 110 is also within this fabrication plane. The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. The distinction between the target particles and non-target material may be made in laser interrogation region 101. There may be a plurality of laser interrogation regions 101, although only one is shown in FIG. 1. Details as to this detection mechanism are well known in the literature, and further discussed below with respect to FIG. 19. However, other sorts of distinguishing signals may be anticipated, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the input stream passes unimpeded to an output orifice and channel 140 which is out of the plane of the sample inlet channel 120, and thus out of the fabrication plane of the device 10. That is, the flow is from the sample inlet channel 120 to the output orifice 140, from which it flows substantially vertically, and thus orthogonally to the sample inlet channel 120. This output orifice 140 leads to an out-of-plane channel that may be perpendicular to the plane of the paper showing FIG. 1, and depicted in the cross sectional views of FIGS. 4a-4c. More generally, the output channel 140 is not parallel to the plane of the sample inlet channel 120 or sort channel 122, or the fabrication plane of the movable member 110.

The output orifice 140 may be a hole formed in the fabrication substrate, or in a covering substrate that is bonded to the fabrication substrate. A relieved area above and below the sorting valve or movable member 110 allows fluid to flow above and below the movable member 110 to output orifice 140, and shown in more detail in FIGS. 4a-4c. Further, the valve 110 may have a curved diverting surface 112 which can redirect the flow of the input stream into a sort output stream, as described next with respect to FIG. 2. The contour of the orifice 140 may be such that it overlaps some, but not all, of the sample inlet channel 120 and sort channel 122. By having the contour 112 overlap the sample inlet channel, and with relieved areas described above, a route exists for the input stream to flow directly into the waste orifice 140 when the movable member or valve 110 is in the un-actuated waste position.

Figure 2:
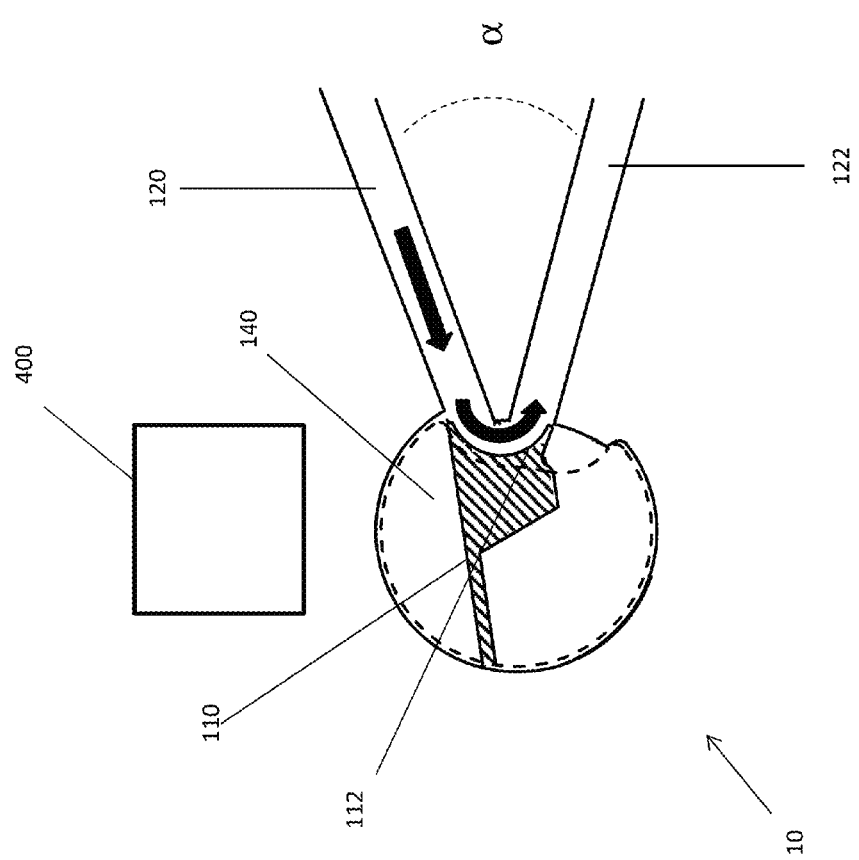
FIG. 2 is a simplified plan view of a microfabricated particle sorting system in the actuated (sort) position.

FIG. 2 is a plan view of the microfabricated device 10 in the actuated position. In this position, the movable member or valve 110 is deflected upward into the position shown in FIG. 2. The diverting surface 112 is a sorting contour which redirects the flow of the sample inlet channel 120 into the sort output channel 122. The output sort channel 122 may lie in substantially the same plane as the sample inlet channel 120, such that the flow within the sort channel 122 is also in substantially the same plane as the flow within the sample inlet channel 120. There may be an angle α between the sample inlet channel 120 and the sort channel 122, This angle may be any value up to about 90 degrees. Actuation of movable member 110 may arise from a force from force-generating apparatus 400, shown generically in FIG. 2. In some embodiments, force-generating apparatus may be an electromagnet, however, it should be understood that force-generating apparatus may also be electrostatic, piezoelectric, or some other means to exert a force on movable member 110, causing it to move from a first position (FIG. 1) to a second position (FIG. 2).

More generally, the micromechanical particle manipulation device shown in FIGS. 1 and 2 may be formed on a surface of a fabrication substrate, wherein the micromechanical particle manipulation device may include a microfabricated, movable member 110 having a first diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface, and a plurality of output channels 122, 140 into which the microfabricated member diverts the fluid, and wherein the flow in at least one of the output channels 140 is not parallel to the plane, and wherein at least one output channel 140 is located directly below at least a portion of the movable member 110 over at least a portion of its motion.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. As shown in FIGS. 1 and 2, the micromechanical particle manipulation device 10 has a first diverting surface 112 with a smoothly curved shape, wherein the surface which is substantially tangent to the direction of flow in the sample inlet channel at one point on the shape and substantially tangent to the direction of flow of a first output channel at a second point on the shape, wherein the first diverting surface diverts flow from the sample inlet channel into the first output channel when the movable member 110 is in the first position, and allows the flow into a second output channel in the second position.

In other embodiments, the overall shape of the diverter 112 may be circular, triangular, trapezoidal, parabolic, or v-shaped for example, but the diverter serves in all cases to direct the flow from the sample inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "sample inlet channel" 120 and "sort channel" 122 may be reversed. The terms used to designate the three channels are arbitrary, but the inlet stream may be diverted by the valve 110 into either of two separate directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

Figure 3B:
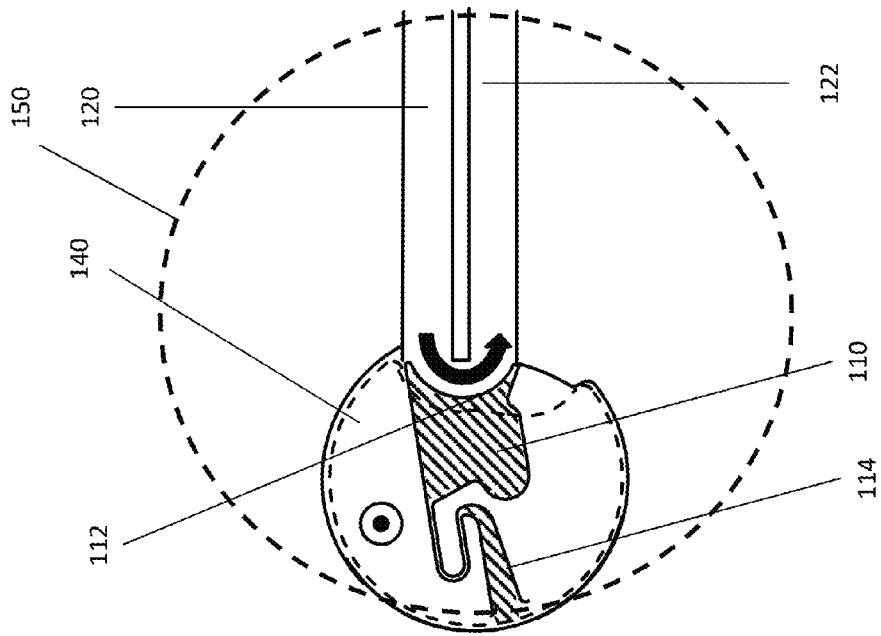
FIG. 3b is a simplified illustration of a microfabricated particle sorting system showing the field of view of the detector, with the microfluidic valve in the actuated (sort) position.
Figure 3A:
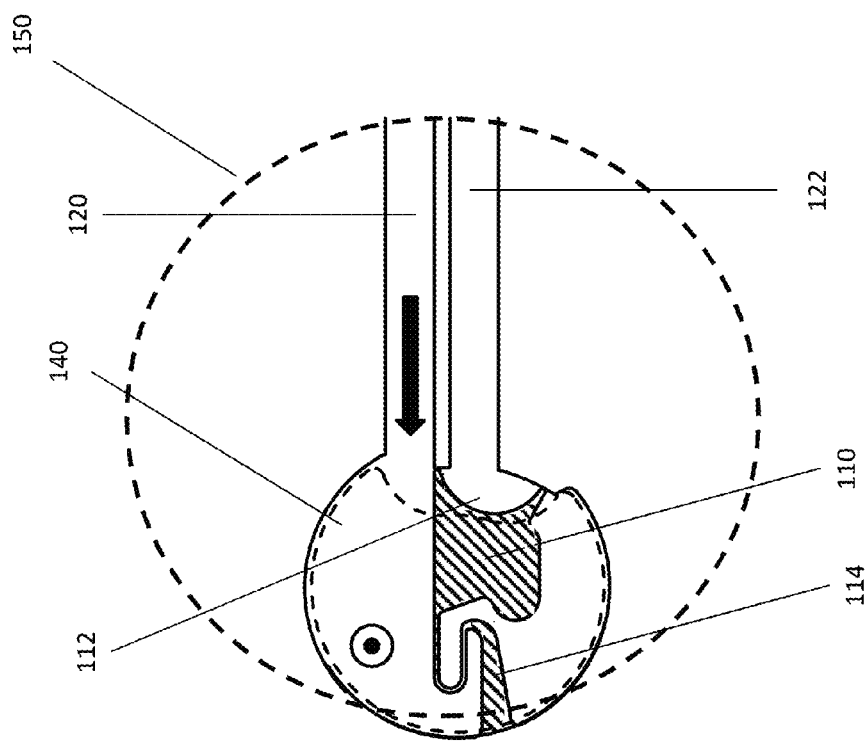
FIG. 3a is a simplified plan view of a microfabricated particle sorting system showing the field of view of the detector, with the microfluidic valve in the quiescent (no sort) position.

FIGS. 3a and 3b illustrate an embodiment wherein the angle α between the sample inlet channel 120 and the sort channel 122 is approximately zero degrees. Accordingly, the sort channel 122 is essentially antiparallel to the sample inlet channel 120, such that the flow is from right to left in the sample inlet channel 120. With valve 110 in the un-actuated, quiescent position shown in FIG. 3a, the inlet stream flows straight to the waste orifice 140 and vertically out of the device 10.

In FIG. 3b, the valve 110 is in the actuated, sort position. In this position, the flow is turned around by the diverting surface 112 of the valve 110 and into the antiparallel sort channel 122. This configuration may have an advantage in that the field of view of the detector 150 covers both the sample inlet channel 120 and the sort channel 122. Thus a single set of detection optics may be used to detect the passage of a target particle through the respective channels. It may also be advantageous to minimize the distance between the detection region and the valve 110, in order to minimize the timing uncertainty in the opening and closing of the valve.

The movable member or valve 110 may be attached to the substrate with a flexible spring 114. The spring may be a narrow isthmus of substrate material. In the example set forth above, the substrate material may be single crystal silicon, which is known for its outstanding mechanical properties, such as its strength, low residual stress and resistance to creep. With proper doping, the material can also be made to be sufficiently conductive so as to avoid charge build up on any portion of the device, which might otherwise interfere with its movement. The spring may have a serpentine shape as shown, having a width of about 1 micron to about 10 microns and a spring constant of between about 10 N/m and 100 N/m, and preferably about 40 N/m FIGS. 4a, 4b, 4c are cross sectional views illustrating the operation of the out-of-plane waste channel 140. FIG. 4c is slightly enlarged relative to FIGS. 4a and 4b, in order to show detail of the flow around the movable member 110 and into the waste channel 142 through waste orifice 140. In this embodiment, the waste channel 142 is vertical, substantially orthogonal to the inlet stream 120 and sort stream 122. It should be understood that other embodiments are possible other than orthogonal, but in any event, the flow into waste channel 142 is out of the plane of the flow in the sample inlet channel 120 and/or sort channel 122. As shown in FIG. 4a, with the valve in the sort, actuated position, the inlet stream and target particle may flow into the sort stream, which in FIG. 4a is out of the paper, and the waste orifice 140 is largely, though not completely, blocked by the movable member 110. The area 144 (shown more clearly in FIG. 4c) on top of the valve or movable member 110 may be relieved to provide clearance for this flow.

When the valve or movable member 110 is un-actuated as in FIG. 4b, the flow of the sample inlet channel 120 may flow directly into the waste channel 142 by going over, around or by the movable member or valve 110. The area 144 on top of the valve or movable member 110 may be relieved to provide clearance for this flow. The relieved area 144 is shown in greater detail in the enlarged FIG. 4c. Thus, when the movable member 110 is un-actuated, the flow will be sent directly to the waste channel. When the movable member 110 is actuated, most of the fluid will be directed to the sort channel, although liquid may still flow over and under the movable member 110.

Thus, the purpose of providing flow both under and over the movable member 110 is to reduce the fluid pressure produced by the actuator motion in the region behind the valve or movable member 110. In other words, the purpose is to provide as short a path as possible between the high pressure region in front of the valve 110 and the low pressure region behind the valve. This allows the valve to operate with little pressure resisting its motion. As a result, the movable valve 110 shown in FIGS. 1-4c may be substantially faster than valves which have all channels disposed in the same plane.

Another advantage of the vertical waste channel 142 is that by positioning it directly underneath a stationary permeable feature 130 and movable permeable feature 116, the magnetic gap between the permeable features 116 and 130 can be narrower than if the fluidic channel went between them. The narrower gap enables higher forces and thus faster actuation compared to prior art designs. A description of the magnetic components and the magnetic actuation mechanism will be given next, and the advantages of the out-of-plane channel architecture will be apparent.

FIG. 5 is a plan view of another exemplary embodiment of device 100 of the device 10, showing the disposition of a stationary permeable feature 130 and further detail of the movable member 110. In this embodiment, the movable member 110 may include the diverting surface 112, the flexible hinge or spring 114, and a separate area 116 circumscribed but inside the line corresponding to movable member 110. This area 116 may be inlaid with a permeable magnetic material such as nickel-iron permalloy, and may function as described further below.

A magnetically permeable material should be understood to mean any material which is capable of supporting the formation of a magnetic field within itself. In other words, the permeability of a material is the degree of magnetization that the material obtains in response to an applied magnetic field.

The terms "permeable material" or "material with high magnetic permeability" as used herein should be understood to be a material with a permeability which is large compared to the permeability of air or vacuum. That is, a permeable material or material with high magnetic permeability is a material with a relative permeability (compared to air or vacuum) of at least about 100, that is, 100 times the permeability of air or vacuum which is about $1.26 \times 10^{-6}$ $H \cdot m^{-1}$. There are many examples of permeable materials, including chromium (Cr), cobalt (Co), nickel (Ni) and iron (Fe) alloys. One popular permeable material is known as Permalloy, which has a composition of between about 60% and about 90% Ni and 40% and 10% iron. The most common composition is 80% Ni and 20% Fe, which has a relative permeability of about 8,000.

It is well known from magnetostatics that permeable materials are drawn into areas wherein the lines of magnetic flux are concentrated, in order to lower the reluctance of the path provided by the permeable material to the flux. Accordingly, a gradient in the magnetic field urges the motion of the movable member 110 because of the presence of inlaid permeable material 116, towards areas having a high concentration of magnetic flux. That is, the movable member 110 with inlaid permeable material 116 will be drawn in the direction of positive gradient in magnetic flux.

Figure 7:
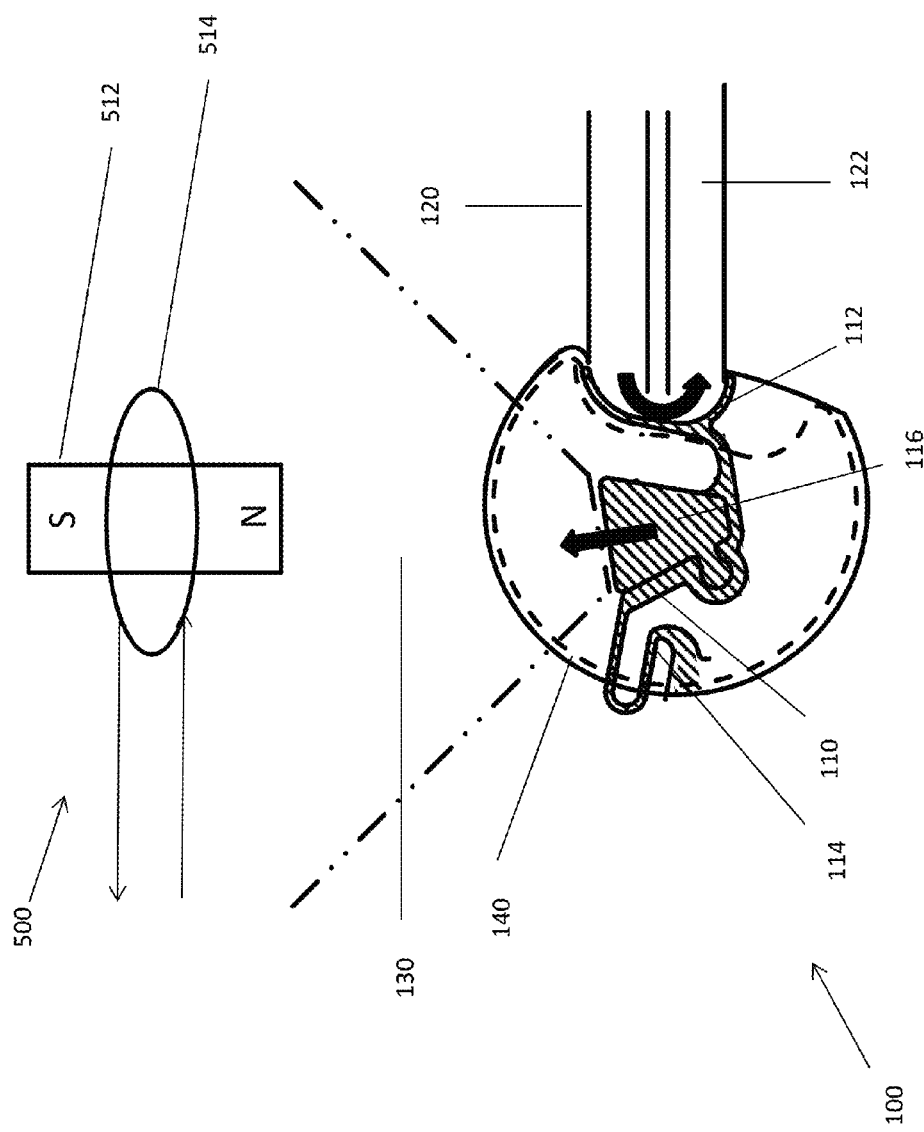
FIG. 7 is a plan view of the actuation mechanism for the microfabricated particle sorting system, showing the functioning of the external magnetic field in combination with the stationary magnetically permeable feature, in the actuated (sort) position.

An external source of magnetic field lines of flux may be provided outside the device 100, as shown in FIG. 6. This source may be an electromagnet 500. The electromagnet 500 may include a permeable core 512 around which a conductor 514 is wound. The wound conductor or coil 514 and core 512 generate a magnetic field which exits the pole of the magnet, diverges, and returns to the opposite pole, as is well known from electromagnetism. Accordingly, the movable member 110 is generally drawn toward the pole of the electromagnet 500 as shown in FIG. 7.

However, the performance of the device 100 can be improved by the use of a stationary permeable feature 130. The term "stationary feature" should be understood to mean a feature which is affixed to the substrate and does not move relative to the substrate, unlike movable member or valve 110. A stationary permeable feature 130 may be shaped to collect these diverging lines of flux and refocus them in an area directly adjacent to the movable member 110 with inlaid permeable material. The stationary permeable feature 130 may have an expansive region 132 with a narrower throat 134. The lines of flux are collected in the expansive region 132 and focused into and out of the narrow throat area 134. Accordingly, the density of flux lines in the throat area 134 is substantially higher than it would be in the absence of the stationary permeable feature 130. Thus, use of the stationary permeable feature 130 though optional, allows a higher force, faster actuation, and reduces the need for the electromagnet 500 to be in close proximity to the device 10. From the narrow throat area 134, the field lines exit the permeable material and return to the opposite magnetic pole of the external source 500. But because of the high concentration of field lines in throat area 134, the permeable material 116 inlaid into movable member 110 may be drawn toward the stationary permeable feature 130, bringing the rest of movable member with it.

When the electromagnet is quiescent, and no current is being supplied to coil 514, the restoring force of spring 114 causes the movable member 110 to be in the "closed" or "waste" position. In this position, the inlet stream passes unimpeded through the device 100 to the waste channel 140. This position is shown in FIG. 5. When the electromagnet 500 is activated, and a current is applied through coil 514, a magnetic field arises in the core 512 and exits the pole of the core 512. These lines of flux are collected and focused by the stationary permeable feature 130 and focused in the region directly adjacent to the throat 134. As mentioned previously, the permeable portion 116 of the movable member 110 is drawn toward the throat 134, thus moving the movable member 110 and diverting surface 112 such that the inlet stream in sample inlet channel 120 is redirected to the output or sort channel 122. This position is shown in FIG. 7.

Permalloy may be used to create the permeable features 116 and 130, although it should be understood that other permeable materials may also be used. Permalloy is a well known material that lends itself to MEMS lithographic fabrication techniques. A method for making the permeable features 116 and 130 is described further below.

As mentioned previously, having the waste channel 140 and 142 directly beneath the movable member or valve 110 allows the movable permeable feature 116 to be disposed much closer to the stationary permeable feature 130. If instead the waste channel were in the same plane, this gap would have to be at least large enough to accommodate the waste channel, along with associated tolerances. As a result, actuation forces are higher and valve opening and closing times are much shorter. This in turn corresponds to either faster sorting or better sorting accuracy, or both.

With the use of the electromagnetic actuation technique described above, actuation times on the order of 10 microseconds can be realized. Accordingly, the particle sorting device is capable of sorting particles at rates in excess of 50 kHz or higher, assuming 10 microseconds required to pull the actuator in, and 10 microseconds required to return it to the as-manufactured position.

Figure 8:
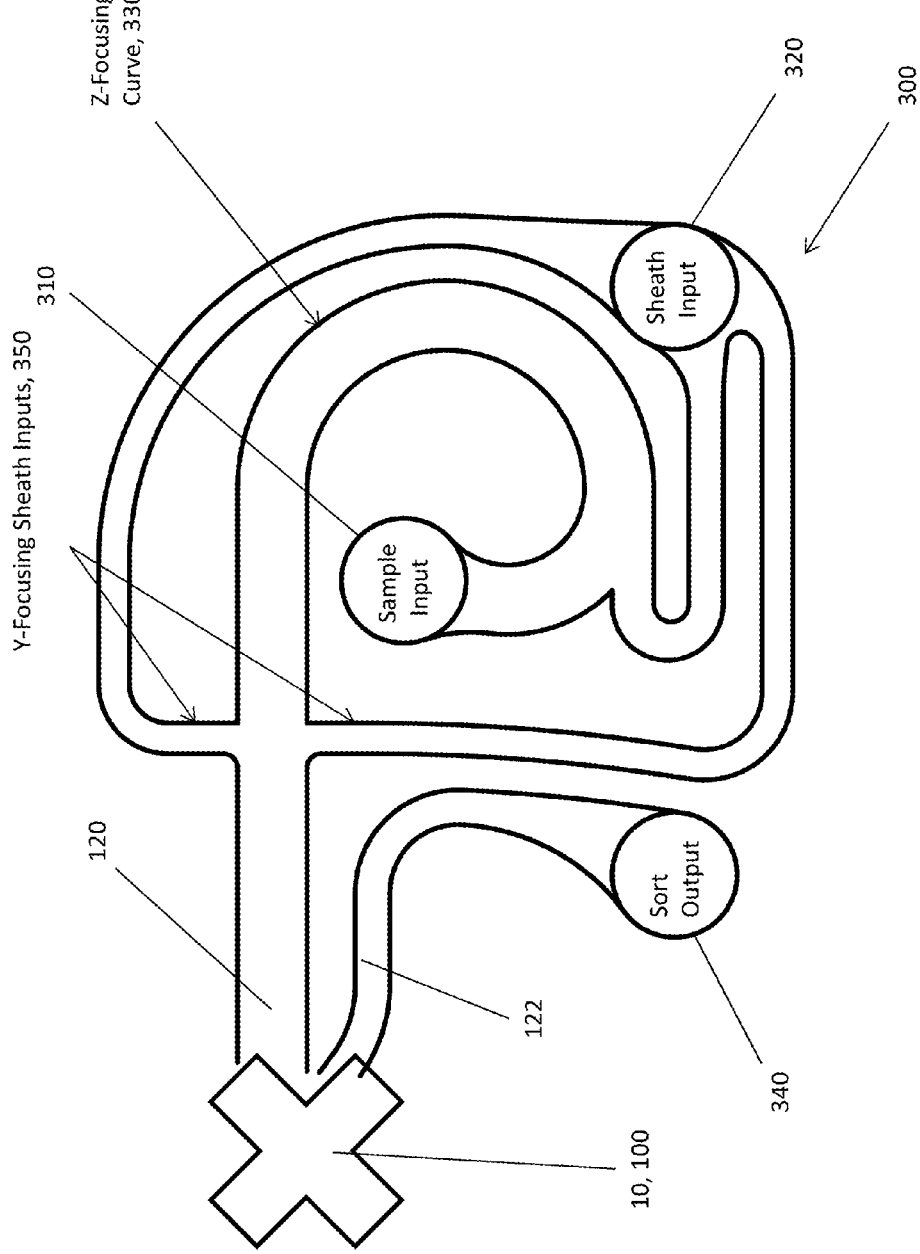
FIG. 8 is a plan view of the microfabricated particle sorting system in combination with a hydrodynamic focusing manifold.

Because of the microfabricated nature of particle manipulation device 10 and 100, it lends itself to techniques that can make use of such an enclosed, well defined architecture. One such technique is illustrated in FIG. 8, wherein the microfabricated particle manipulation device may be coupled to a microfabricated fluidic focusing element 300. The focusing element 300 may include at least one additional sheath fluid inlet channel 320 that provides a sheath fluid to the sample stream and also a z-focusing curve 330 coupled to the sheath fluid inlet channel 320. The sheath fluid may be used to adjust the concentration or positioning of the target particles within the sample inlet channel. The focusing element 300 may be configured to urge the target particles into a particular portion of the sample inlet channel 120, such that the sorting process has fewer errors, as described further below.

The focusing element 300 may be disposed in substantially the same plane as the movable member 110, and may be formed in the same substrate surface as the movable member 110 and sample inlet channel 120. The focusing element 300 may rely on inertial forces to focus the particles, as will be described further below. These forces may require relatively large flow rates to be effective. The microfabricated particle manipulation system with out-of-plane channel may be particularly suited to such an inertial focusing device, because of the narrow channels and high flow rates.

FIG. 8 depicts the microfabricated focusing element 300 which may be used to focus the particles in a certain area within the fluid stream. As the name suggests, the sheath fluid inlet channel 320 adds a sheath fluid to the sample stream, which is a buffering fluid which tends to dilute the flow of particles in the stream and locate them in a particular portion of the stream. The combined fluid then flows around a focusing element 300 coupled to the sample inlet channel 120. The focusing element 300 may include here a z-focusing curve 330, which tends to herd the particles into a particular plane within the flow. This plane is substantially in the plane of the paper of FIG. 8. The combined fluid in the focusing element 300 then passes another intersection point, a "y-intersection point" 350, which introduces additional sheath fluid above and below the plane of particles. At the y-intersection point 350, two flows may join the z-focus channel 330 from substantially antiparallel directions, and orthogonal to the z-focus channel 330. This intersection may compress the plane of particles into a single point, substantially in the center of the stream. Accordingly, at the y-intersection point 350 the target particles may be compressed from a plane to a stream line near the center of the z-focus channel 330 and sample inlet channel 120. Focusing the particles into a certain volume tends to decrease the uncertainly in their location, and thus the uncertainty in the timing of the opening and closing of the movable member or valve 110. Such hydrodynamic focusing may therefore improve the speed and/or accuracy of the sorting operation.

In one exemplary embodiment of the microfabricated particle manipulation device 10 or 100 with hydrodynamic focusing illustrated in FIG. 8, the angular sweep of z-bend 330 is a curved arc of about 180 degrees. That is, the approximate angular sweep between the junction of the sheath fluid inlet channel 320 and the y-intersection point 350, may be about 180 degrees. Generally, the radius of curvature of the z-bend 330 may be at least about 100 microns and less than about 500 microns, and the characteristic dimension, that is the width, of the channels is typically about 50 microns to provide the focusing effect. In one embodiment, the radius of curvature of the channel may be about 250 microns, and the channel widths, or characteristic dimensions, for the sample inlet channel 120 and z-bend channel 330 are on the order of about 50 microns. These characteristic dimensions may provide a curvature sufficient to focus the particles, such that they tend to be confined to the plane of the paper upon exit from the z-focus channel 330 at y-intersection point 350. This plane is then compressed to a point in the channel at the y-intersection point 350. Accordingly, the y-intersection 350 flows along with the z-focusing element 330 may urge the particles into a single stream line near the center of the microfabricated sample inlet channel 120.

Figure 9:
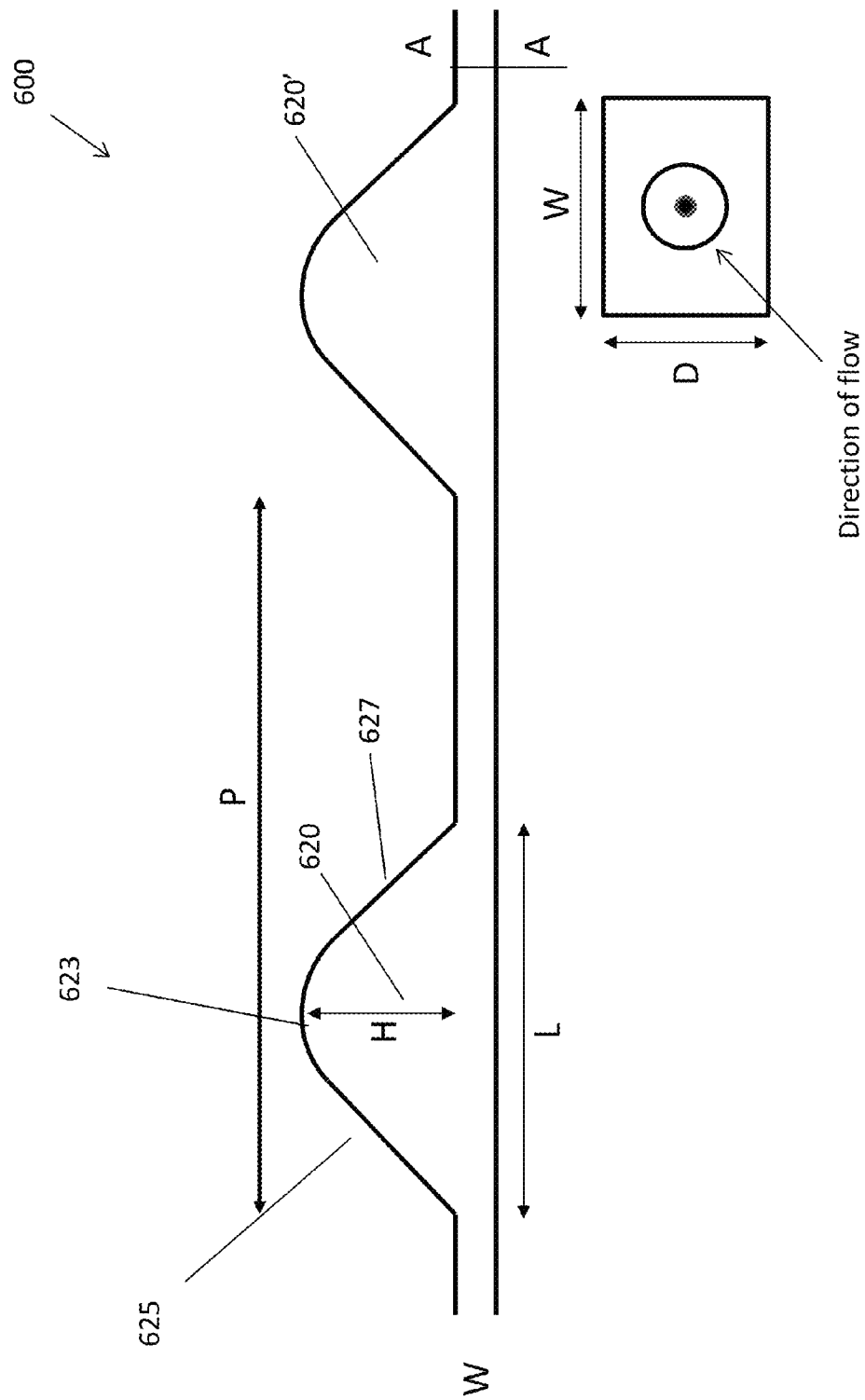
FIG. 9 is simplified schematic diagram of the novel variable cross section focusing channel.

FIG. 9 shows another embodiment of a focusing element, 600. In this embodiment, the focusing element 600 includes a plurality of segments having a variable lateral dimension or cross section. The variable cross section portion of the channel serves to urge or focus the particles into a particular portion of the stream flowing in the channel. The discussion now turns to the design and performance details of this variable cross section focusing channel as applied to the above described microfabricated particle sorter 10, 100.

The novel flow channel may possess portions of variable cross section, wherein the variable cross section arises from the shapes of the sidewalls of the flow channel. These variable portions may have one sidewall which is substantially straight with respect to the flow direction, and an adjacent side wall which is not straight, or at least not parallel to the substantially straight portion. In particular, this adjacent sidewall may be triangular or parabolic in shape, deviating away from the straight sidewall in an expanding region, to a point of maximum channel width, before coming back to the nominal distance between the sidewalls in a contracting region. The expanding portion, maximum point, and contracting portion may constitute what is hereafter referred to as a fluid "cavity" 620 in the microfabricated channel. Accordingly, the variable channel width segments may define expansion/contraction cavities 620, 620' within the microfluidic channel, wherein the cavity is defined by the expanding portion followed by the contracting portion.

The cavity 620 should be understood to be in fluid communication with the microfabricated fluid channel, such as sample inlet channel 120, such that fluid flows into and out of the cavity 620. It should be understood that this cavity 620 may be a two-dimensional widening of the channel in the expanding region, and narrowing of the channel in the contracting region. This shape of geometry is shown schematically in FIG. 9.

The variable cross section focusing channel 600 may be used instead of the curved focusing channel 300 shown in FIG. 8. That is, the variable crass section focusing channel 600 may be used in place of the z-focusing curve 330, or in place of the entire focusing element 300. The variable cross section focusing element 600 may be disposed upstream of the moveable member sorting device 110.

The cavity 620 may have a length of L, which may be the distance between the expanding and contracting portions. More particularly, the variable cross section portion, cavity 620, may have an expanding region 625 and a contracting region 627 disposed over a distance L with a high point 623 between them. The high point 623 may be the point of maximum lateral extent of the channel 600, that is, the portion of widest channel width. As shown in FIG. 9, the variable cross section focusing channel 600 may include a plurality of expanding and contracting regions, such as 620 and 620' shown in FIG. 9. The expanding and contracting regions may be arranged in different ways with respect to a turn that is made by the channel as it directs the sample fluid from the sample input 310 to the valve mechanism 10 or 110.

Because of this shape, and expanding region 625 followed by a contracting region 627, the variable cross section focusing channel 600 may encourage various eddies, motions and hydrodynamic forces within the focusing element.

FIG. 9 illustrates quantities that will used to discuss the various design parameters and their resulting hydrodynamic behaviors in further detail below. H is the height of the variable cross section portion cavity, and L is the length of the cavity portion. W is the nominal width of the sample inlet channel 120 (channel without the expanding and contracting cavities). H/W is the aspect ratio of the variable cross section cavity portion with respect to the nominal channel width. The pitch P is the distance between one cavity 620 and a subsequent cavity 620'. The following design aspects are discussed in detail below: Cavity pitch (P/H), cavity size (H/W), aspect ratio (W/D) and valve positioning. The performance of the variable cross section focusing element 600 will then be discussed with respect to these design choices.

Figure 10:
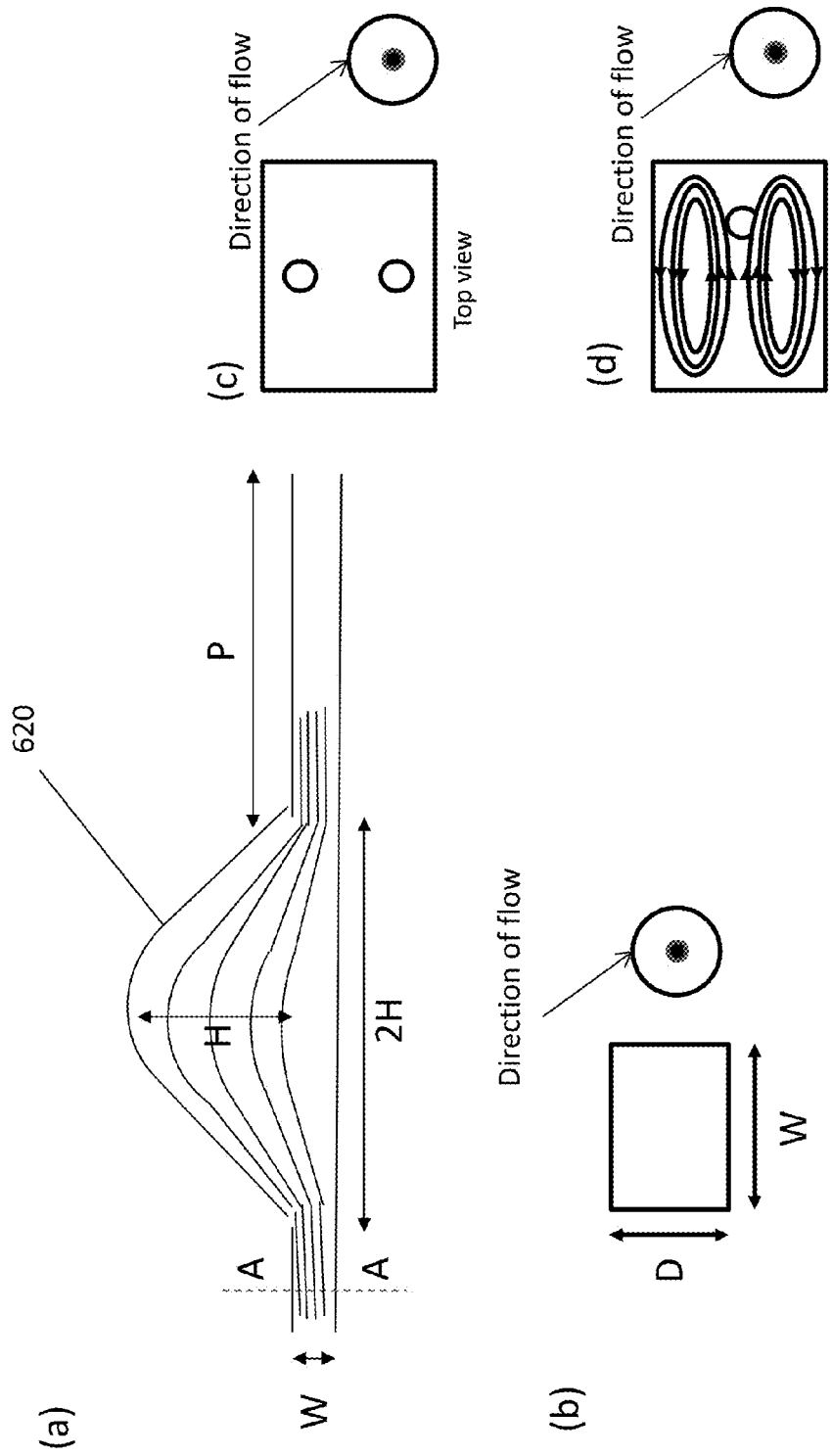
FIG. 10 is simplified schematic diagram of the forces operating in the novel variable cross section focusing channel; (a) shows the contours of the device and th streamlines therein; (b) shows the cross sectional dimensions and the flow direction; (c) shows the stable regions in the flow; and (d) shows the hydrodynamic forces acting on the particles.

As mentioned previously, various hydrodynamic effects may result from this variable cross section geometry, and these are illustrated in FIG. 10. These effects may result in a geometry induced secondary flow focusing. Particles experience two forces in the flow. The first may be an inertial lift force, which is a combination of shear gradient lift resulting from the flow profile parabolic nature, and wall lift force. In addition, the particles may experience Dean flow drag: which is the drag force exerted on the particle as a result of the secondary dean flow induced by curved streamlines. It is possible to balance these two forces by proper selection of the geometrical parameters of height, size, aspect ratio and placement. Accordingly, these two forces may be balanced by introduction of the expansion-contraction cavities 620 of a particular size, shape and distribution, in the variable cross section element 600. The combination of geometrical parameters determines whether there is a balance between these forces or not and where in the channel are the equilibrium nodes or points where the net force on the particles is zero.

As a result of these balanced forces, particles may be focused in one position within the channel using the cavities 620, 620' shown in FIG. 9, as the particles are brought to a two dimensional focused state.

FIG. 10 is simplified schematic diagram of the forces operating in the novel variable cross section focusing channel; (a) shows the contours of the device and the streamlines therein; (b) shows the cross sectional dimensions and the flow direction; (c) shows the stable regions (equilibrium nodes) in the flow channel without cavities; and (d) shows the hydrodynamic forces acting on the particles as a result of curved streamlines in the cavities;

As shown in FIG. 10(a), the cavities 620 in focusing element 600 are generally triangular cavities with a height of H and a base of 2H. In other words, the cavities may be two adjacently placed equilateral triangles. The width, W, of the nominal channel before and after the cavities 620 and 620', is used as a scale factor, to parametrize the quantities as discussed below. The apex of the triangle may be smoothed to discourage bubbles becoming trapped at the apex.

The cross section of the channel is shown in (b) along with the flow direction in the channel. The inertial focusing effects are shown in FIG. 10(c). An equilibrium position exists for particles in a straight channel with the same non-varying cross section. The expansion-contraction cavities create an out of plane secondary flow (dean flow) which balances the inertial drag force and changes the equilibrium nodes, as shown in (d). Accordingly, an equilibrium position for the particles will exist as shown in FIG. 10, as shown in (c).

Figure 11:
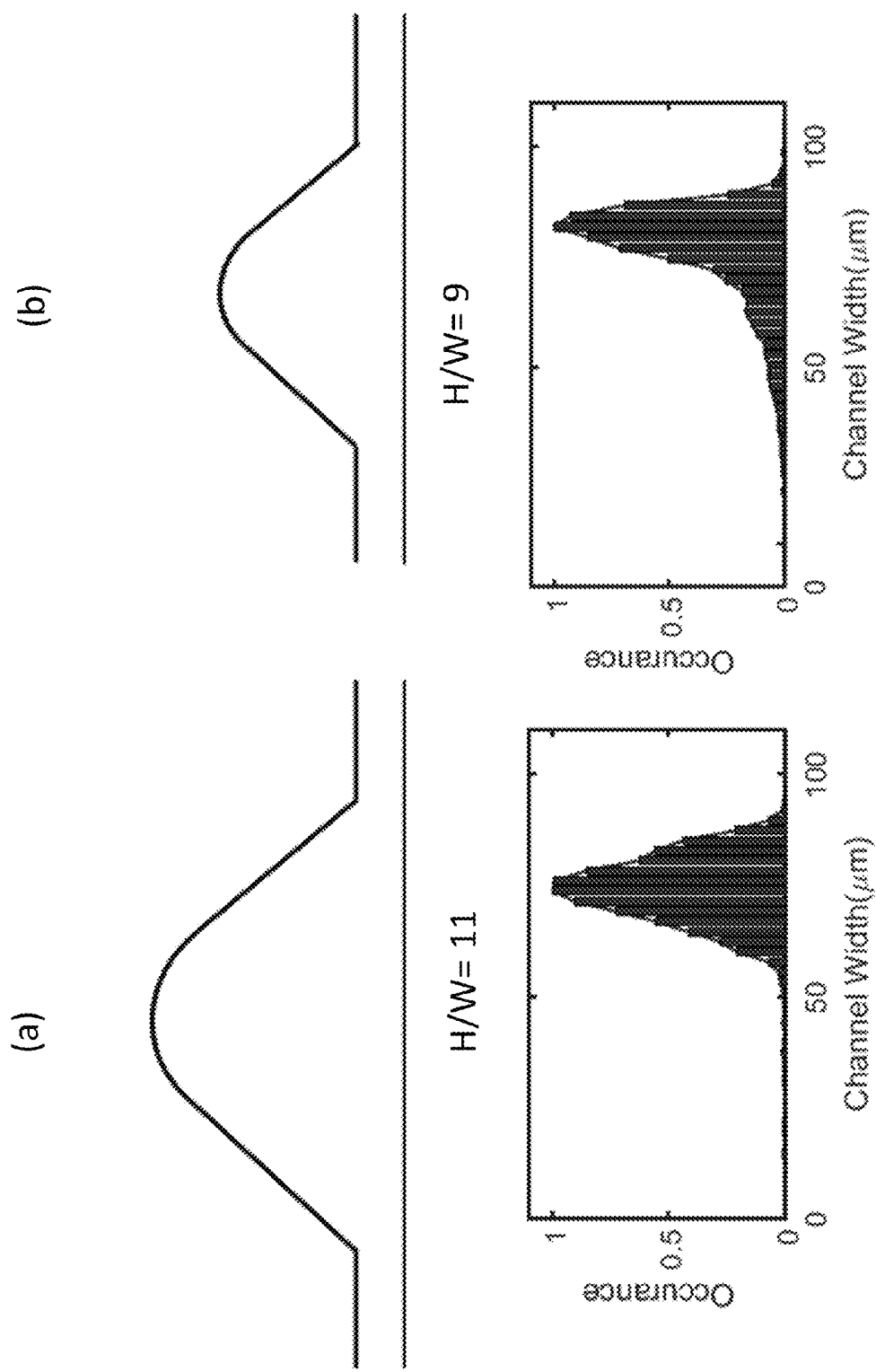
FIG. 11 shows a data plot of the novel variable cross section focusing channel showing the relationship of performance to cavity size; (a) for cavity size H/W=11; and (b) for cavity size H/W=9.

FIG. 11 shows the dependence of this focusing behavior on cavity size. The cavity size is parameterized as H/W where H is the height of the cavity 620 and W is the width of the nominal channel 120. Cavity size determines how the dean flow drag force created as a result of curved streamlines is balanced with the inertial drag force by means of the size of the curvature that is being introduced to the flow. As the cavities become larger, particles experience higher curvature flow streamlines which results in bigger Dean flow drag. Also by increasing the size of the cavities, the effective Dean flow drag increases due to the longer curvature in the flow streamlines. FIG. 11 shows a data plot of the novel variable cross section focusing channel showing the relationship of performance to cavity size: (a) for cavity size H/W=11; and (b) for cavity size H/W=9. Accordingly selection of H/W in the range of 5 to 15 may be suitable for some applications.

Figure 12:
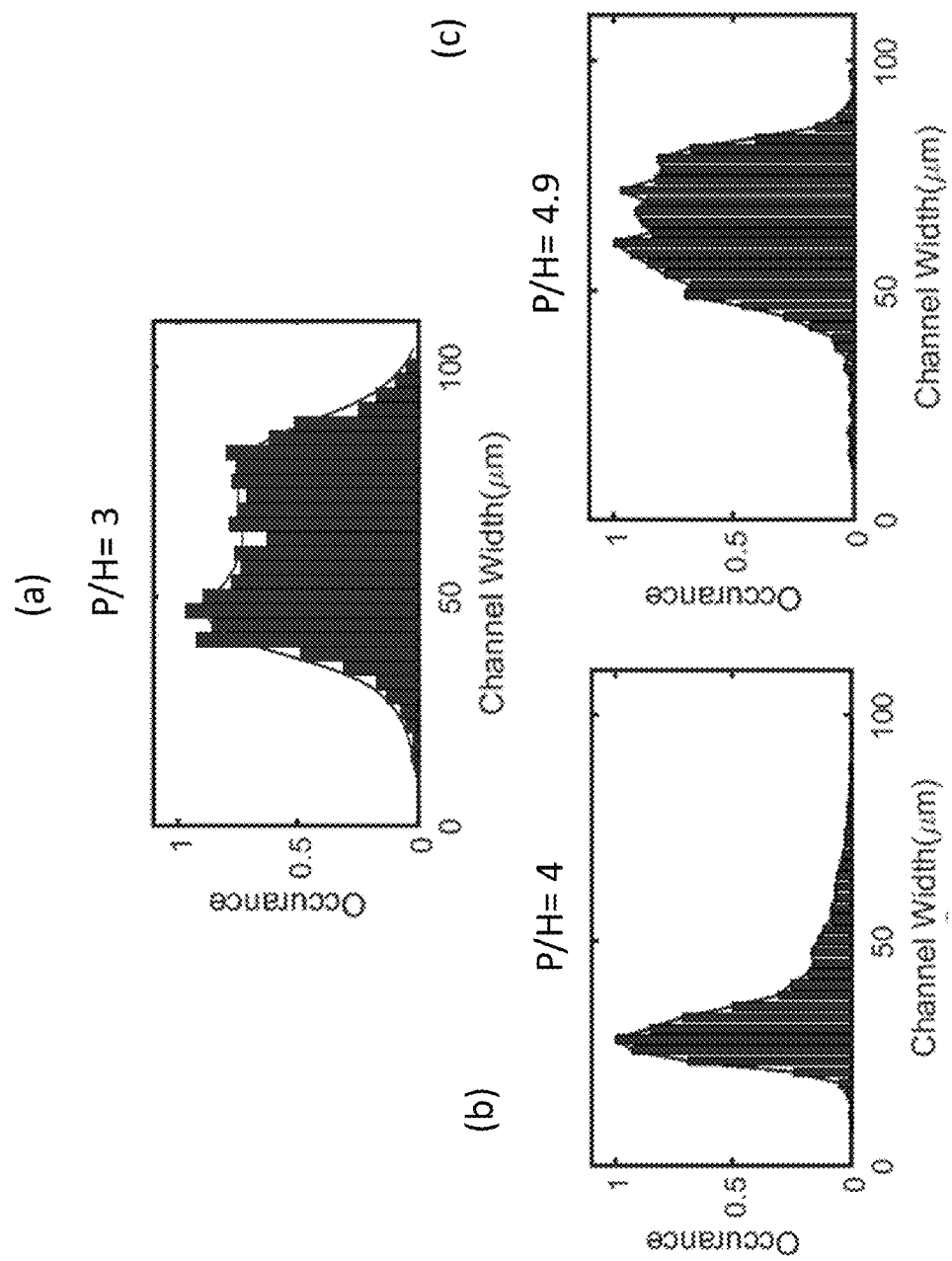
FIG. 12 shows a data plot of the novel variable cross section focusing channel showing the relationship of performance to pitch between the variable portions of the flow channel; (a) for pitch to height of 4; (b) for pitch to height of 3; (c) for pitch to height of 4.9.

FIG. 12 illustrates the dependency of the focusing behavior on the pitch, that is the distance, between the cavities 620 and 620'. Again, the pitch is parameterized by the height of the cavity, i.e. P/H.

Cavity pitch determines the balance between the Dean flow drag (only present in the cavities with curved streamlines) and inertial drag (stronger in the straight section). Since the magnitudes of these forces are of the same order, the length of the straight and curved flow sections has to be balanced in order to focus the particles to equilibrium positions. FIG. 12 shows a data plot of the novel variable cross section focusing channel showing the relationship of performance to pitch between the variable portions of the flow channel: (a) for pitch to height of 4; (b) for pitch to height of 3; (c) for pitch to height of 4.9. It was determined that a cavity pitch on the order of about P/H=4 (1:1 cavity: straight) was the optimum value.

Figure 13:
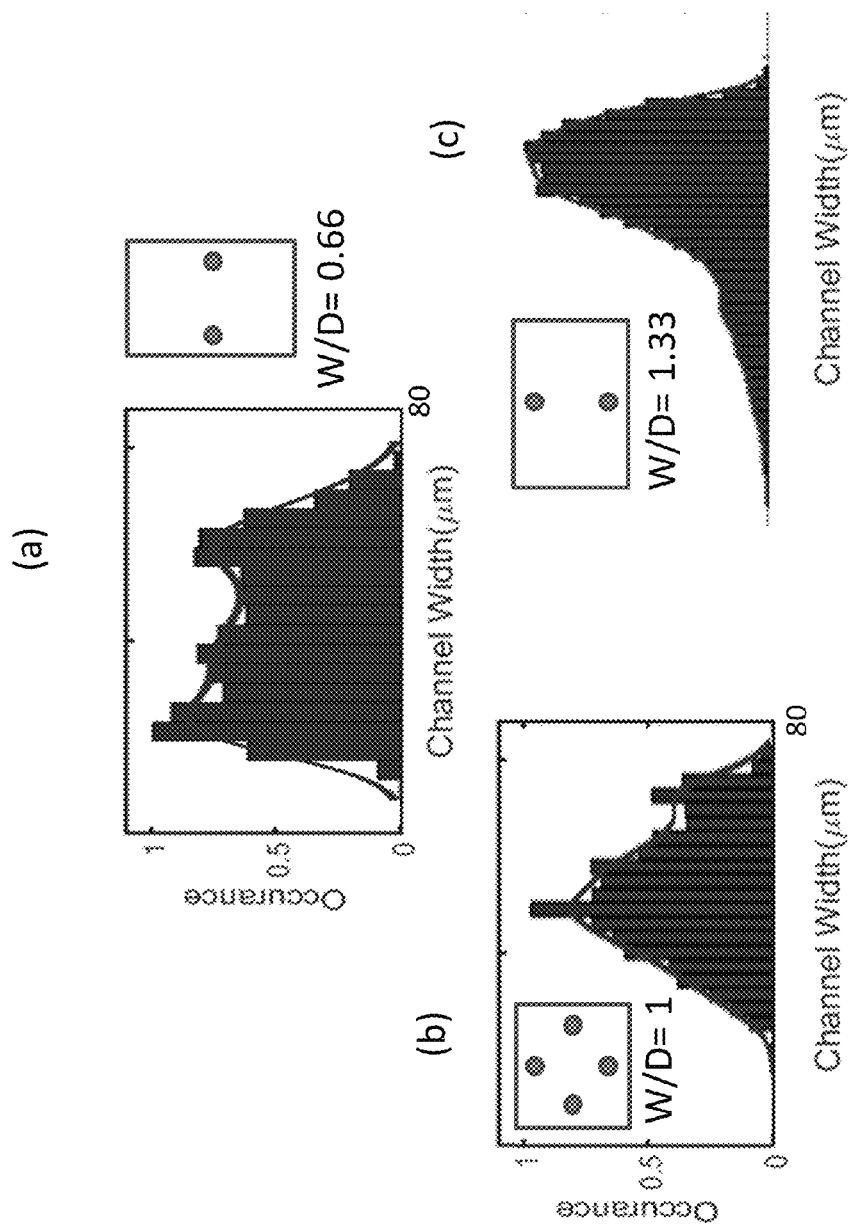
FIG. 13 shows a data plot of the novel variable cross section focusing channel showing the relationship of performance to aspect ratio of the variable portions of the flow channel; (a) for aspect ratio (W/D) of 0.66; (b) for aspect ratio (W/D) of 1.0; (c) for aspect ratio (W/D) of 1.33.

FIG. 13 illustrates the dependency of this behavior on aspect ratio, i.e the height divided by the nominal width of the channel 120. The aspect ratio of the channel determines the nature of the balance between various forces in the flow and how the equilibrium nodes are positioned in the channel cross section. A square channel (AR=1) shown in (b) has four equilibrium positions compared to a rectangular channel, which has only two. Also the rectangular channels with W/D>1(c) and W/D<1 (a) have different equilibrium points with respect to the cavities which results in longer or shorter channel lengths required for them to migrate to equilibrium positions. FIG. 13 shows a data plot of the novel variable cross section focusing channel showing the relationship of performance to aspect ratio of the variable portions of the flow channel: (a) for aspect ratio (W/D) of 0.66; (b) for aspect ratio (W/D) of 1.0; (c) for aspect ratio (W/D) of 1.33. It was determined that an aspect ratio of at least about 1 was superior to aspect ratios W/D<1.

Figure 14:
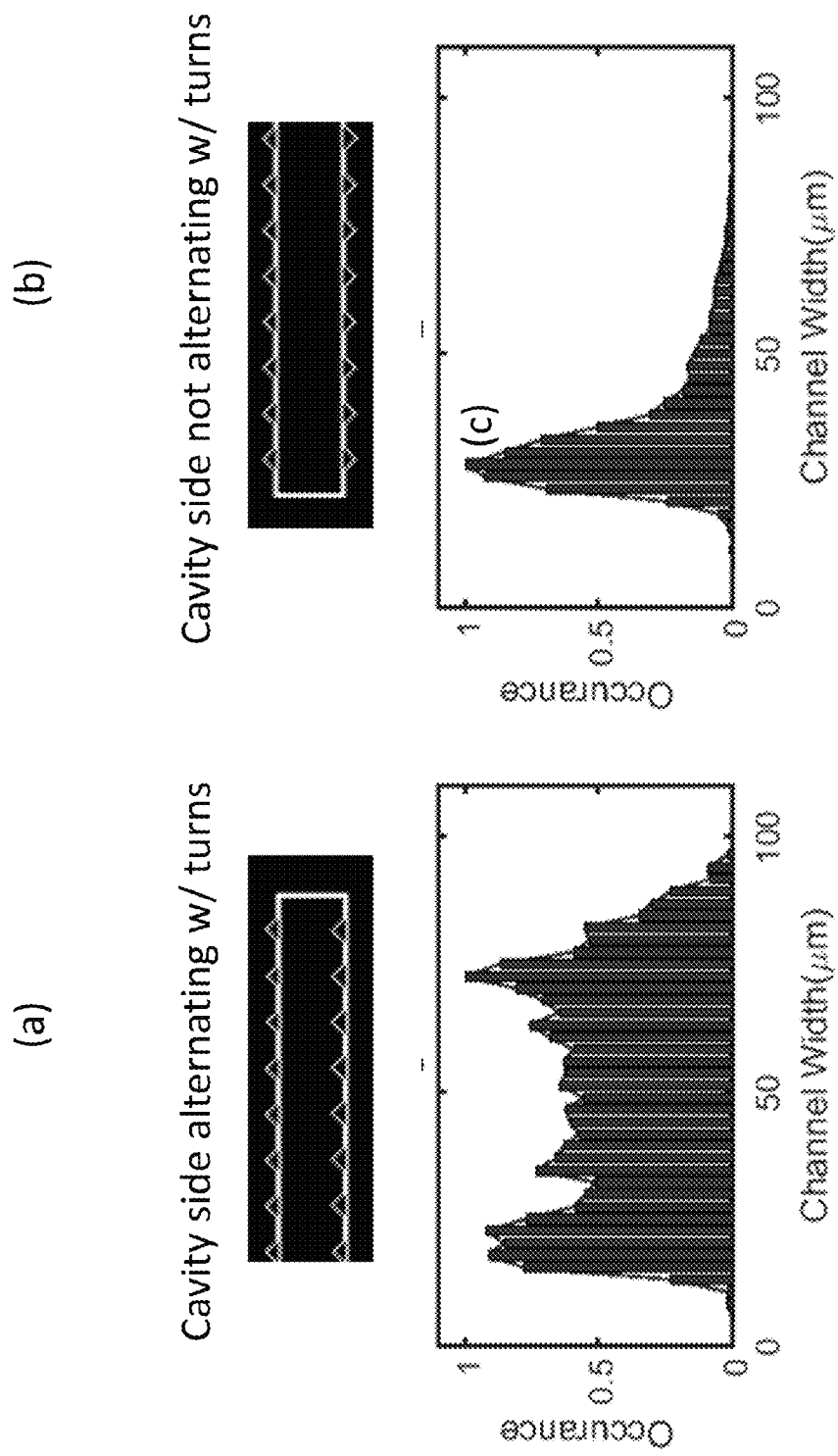
FIG. 14 shows a data plot of the novel variable cross section focusing channel showing the relationship of performance to the locations of the variable portions of the flow channel; (a) for cavities on same side with respect to a turn; (b) with cavities on the outside of the turn.

A compact design is needed, and so the channel will generally be folded serpentine or spiral in order to fit a long effective length into a small space. Therefore, the channel must have turns. FIG. 14 illustrates the dependency of the focusing behavior on the cavity orientation after turns. In other words, determinative may be whether the cavity is widest on the inside wall of the turns or on the outside wall. It was found that by keeping the cavities on the same side of the channel after each turn, the direction of the Dean flow drag force remains consistent before and after the turns. The forces are consistent throughout the length of the channel if the cavities are always on the outside of the turn. As a result the particles may be focused (and thus sorted) more effectively if the cavities are always on an outer wall. It was noted that the channel having alternating cavities, on the inside and outside, functions very poorly.

FIG. 14 shows a data plot of the novel variable cross section focusing channel showing the relationship of performance to the locations of the variable portions of the flow channel; (a) for cavities switching sides before and after a turn; (b) with cavities on the outside of the turn. Cavities on the outside of a turn as in (b) function substantially better.

Ideally, the cavities could be pyramidal or triangular. However it was found that bubbles tend to form at the sharp apex the triangular cavity. Accordingly, the triangular cavities were rounded in order to avoid bubble accumulations and easily push out bubbles. Having the rounded corners significantly reduces the chance of having bubbles in the cavities, given a certain water-contact-angle.

Making the surfaces hydrophilic may also mitigate the bubble accumulation, and especially in conjunction with the rounded corners.

Figure 15:
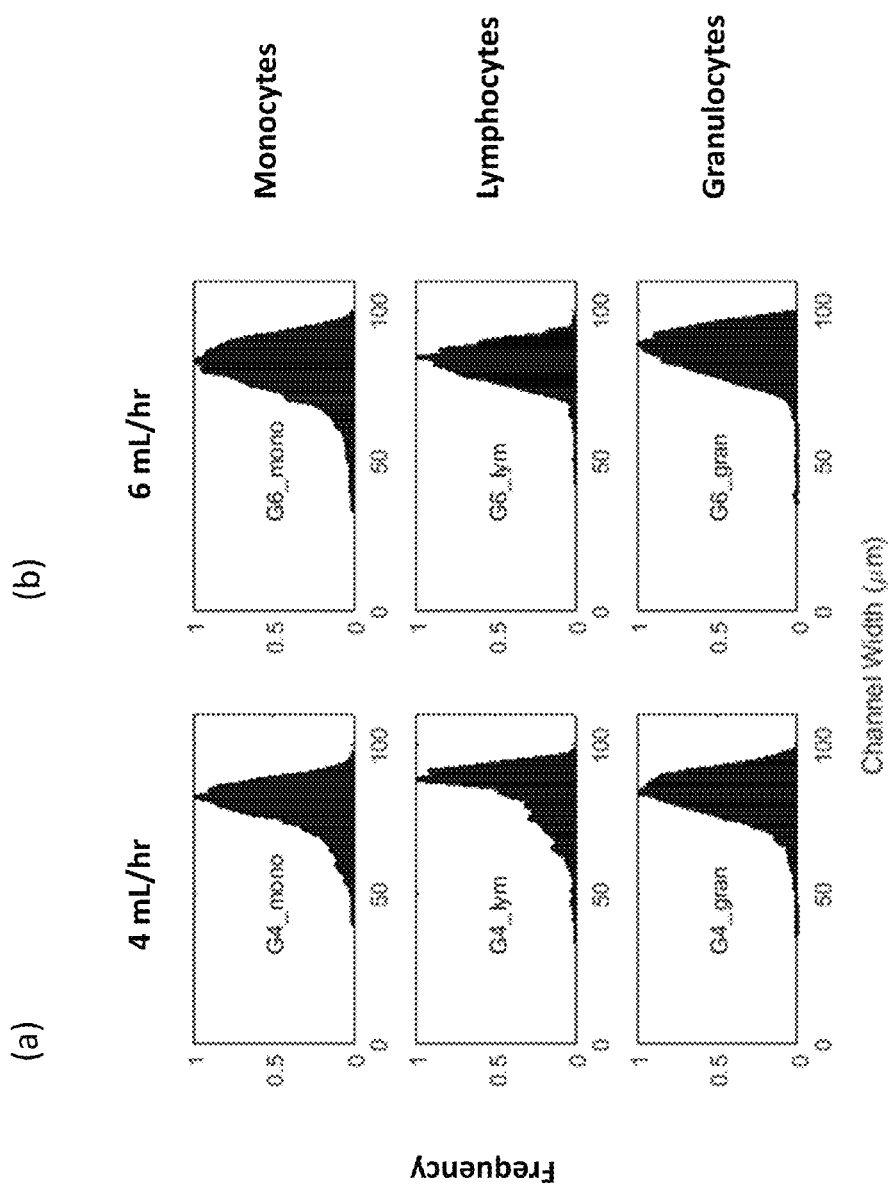
FIG. 15 shows a data plot showing the efficacy of the novel variable cross section focusing channel; (a) at a flow rate of 4 ml/hour and (b) at a flow rate of 6 ml/hour.

FIG. 15 shows the performance the microfabricated cell sorter of FIGS. 6 and 7 with the variable cross section focusing channel shown in FIG. 9, applied to a sample of blood. The microfabricated sorter 10, 100 was operated to separate blood subpopulations from a sample. Isolated sub populations of monocytes, lymphocytes, and granulocytes were introduced to the device to determine the effects of the focusing. Lymphocytes and granulocytes showed similar behavior and different from monocytes. Better focusing can be seen with lymphocytes and granulocytes than monocytes.

FIG. 15 shows a data plot showing the efficacy of the novel variable cross section focusing channel; (a) at a flow rate of 4 ml/hour and (b) at a flow rate of 6 ml/hour. As can be seen in FIG. 15, the sorting performance with the variable cross section is better at elevated flow rates of 6 ml/hour, and especially for lymphocytes and granulocytes.

Figure 16:
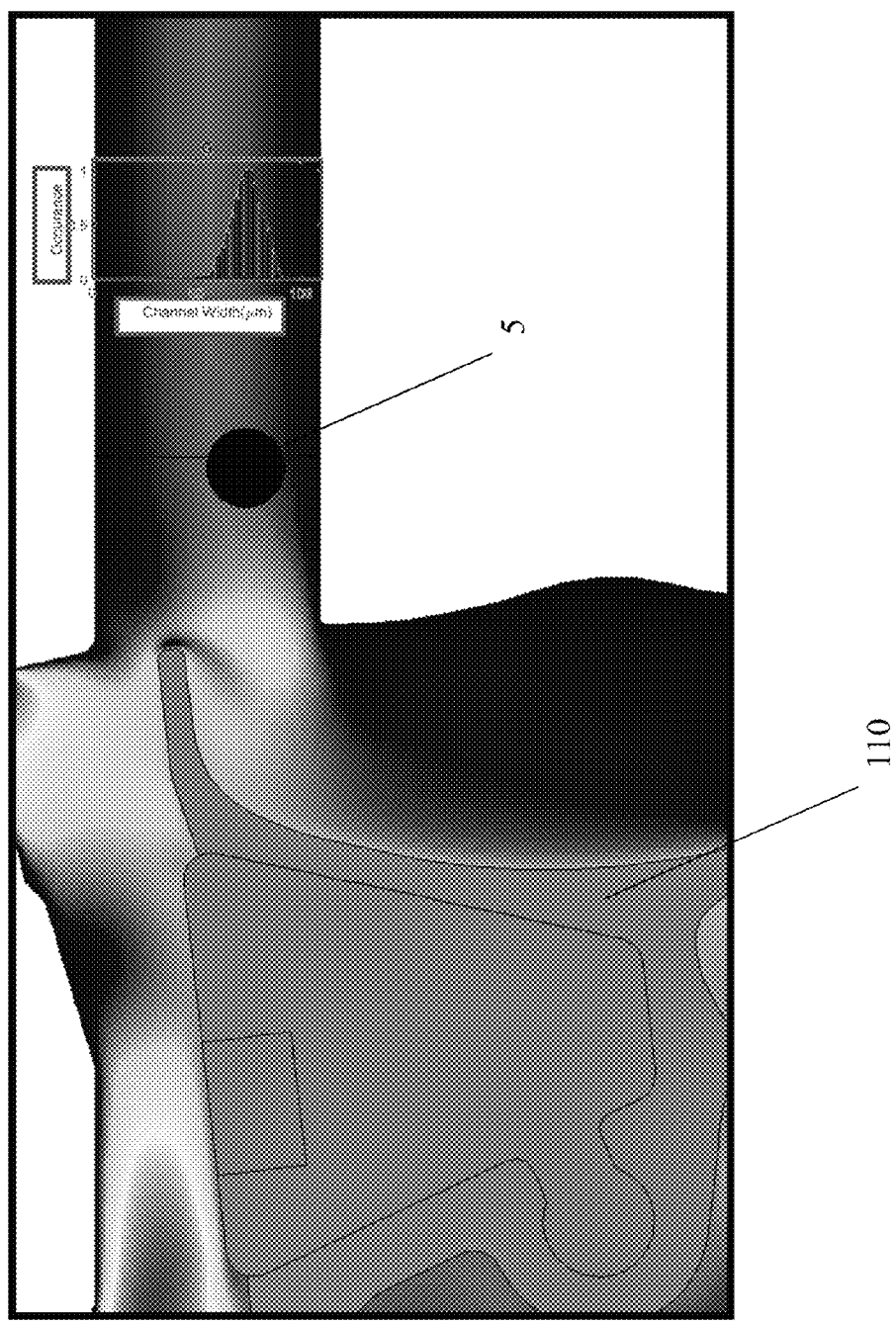
FIG. 16 shows the spatial relationship between the focused particles and the sorting valve.

Lastly, because the variable cross section focusing channel tends to focus the particles into a distinct streamline within the flow channel, it is possible that the placement of the valve 110 can be optimized with respect to this streamline. FIG. 16 shows the effect of this focusing on valve placement. In particular, the focusing element tends to concentrate particles toward the hinge side of the moveable member 110, as illustrated in FIG. 16. Accordingly, the throw designed into the movable member 110 may be somewhat less than that required if there were no focusing and the particles were equally likely to be found anywhere in the sample channel 120. For this reason, the throw of the valve may be reduced, and thus the device may be operated at a faster sorting rate. Sort rate is a primary figure of merit for sorting devices, and thus the focusing has a distinct advantage.

In other words, because the cavities are placed asymmetrically on one side of the channel 120, the device focuses the particle off-center in the across-the-channel dimension and closer to the cavity side. As a result, one can exploit this feature by designing the device such that the particles are focused near the valve home position. As a result, smaller valve opening is required to sort the desired particles. Because smaller motions are required, the valve 110 may open and close more quickly, thus increasing the speed of the device, which is a primary figure of merit for cell sorters.

The histogram inlaid in FIG. 16 shows the distribution of particles across the channel dimension, indicating their concentration on the hinge/cavity side of the channel. Accordingly, the valve needs only to be opened to about ½ of the channel diameter to capture the majority of the particles.

Figure 18:
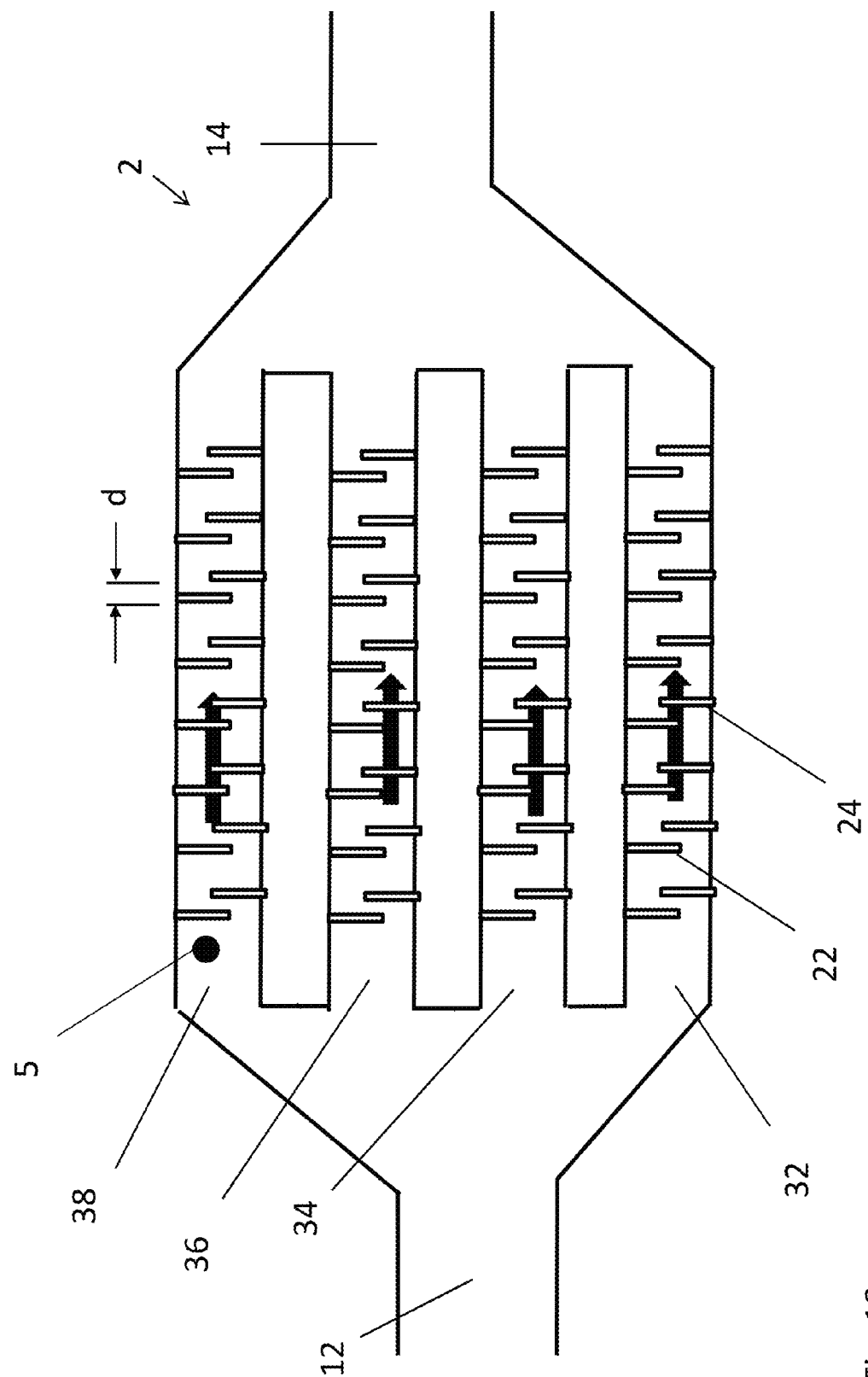
FIG. 18 is a plan view of a microfabricated particle filter that may be used with the microfabricated particle manipulation device described here.

A filter element may be added for the purpose of retaining undesired particles, and placed upstream of the hydrodynamic focusing elements and the movable member 110 of the valve. FIG. 18 shows one such device, with parallel filter elements to allow more filter area and also robustness to filter clogging.

Figure 17:
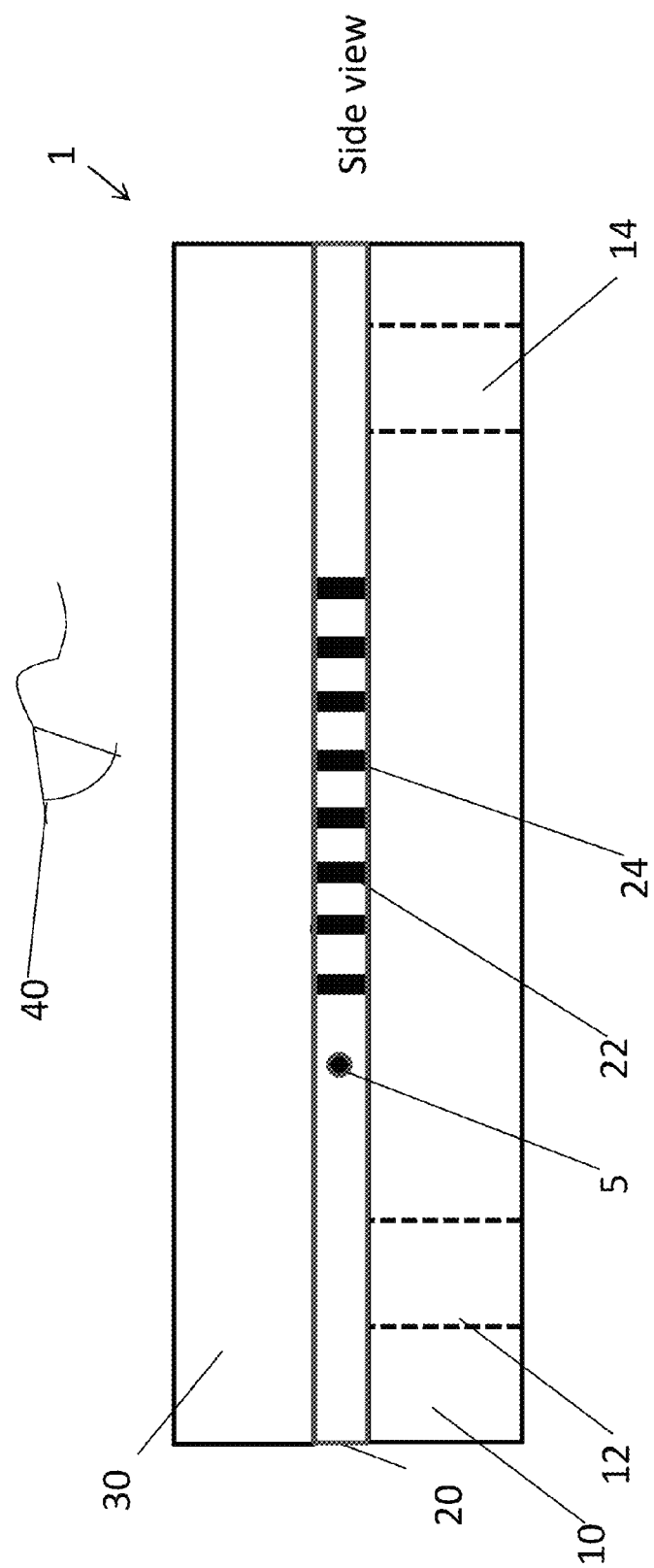
FIG. 17 is a cross sectional view of a microfabricated particle filter that may be used with the microfabricated particle manipulation device described here.

FIG. 17 is a cross sectional illustration of a microfabricated filter. The filter may be used in, for example, a cell sorting system as described below. In FIG. 17, a sample stream may include at least one debris particle 5, suspended therein. The sample stream may be admitted to the filter structure 1 through an inlet channel 12, from which it may flow laterally across the face of the substrate 10 as shown by the arrows in FIG. 18. The flow may traverse a series of filter barriers 22, 24 which are arranged so as not to seal the channel to the flow of the sample stream, but to trap particles of a particular size which may be suspended in the sample stream. In FIGS. 17 and 18, these filter barriers may be disposed in a staggered arrangement across the width of the channel. However, no barriers extend entirely across the channel so as to seal it against the flow. Instead, the sample stream may flow between the staggered barriers 22 and 24 which may be separated by a distance d. Accordingly, particulate debris with a dimension greater than d may be trapped in the filter 1.

As shown in FIG. 17, the microfabricated channel with filter barriers 22, 24 may be sealed on top by another layer or substrate 30. This layer or substrate 30 may be optically transparent, allowing radiation to pass through and impinge upon the trapped particle 5. The transparent layer 30 may comprise at least one of quartz, sapphire, zirconium, ceramic, and glass. The transparent layer 30 may allow analysis and characterization of the particulate debris found in the sample stream. Such information may be important in identifying and correcting the source of the contamination. FIG. 17 shows evaluation of trapped particle 5 by an analysis unit 40, such as a microscope or spectrometer. The analysis technique may include investigation of specular, diffractive, refractive behaviors of the particle 5, for example. Accordingly, the filter system may include an optical microscope which is disposed adjacent to the filter and is configured to image the particulates intercepted by the plurality of barriers, through the transparent layer 30. Alternatively, the analysis tool may be a spectrometer which is disposed adjacent to the filter and is configured to analyze the particulates intercepted by the plurality of barriers, through the transparent layer. In other embodiments, x-ray diffraction, crystallography, or other methods may be used to analyze the trapped debris through the transparently layer 30.

FIG. 18 is a plan view of the microfabricated filter 2. FIG. 18 shows effectively the staggered arrangement of the filter barriers 22 and 24. In one embodiment, each filter barrier 22 extends less than the full diameter, but more than one-half of the diameter of the channel. Accordingly, by staggering pairs of like filter barriers 22, 24 one behind the other, the channel remains open to the passing of the sample stream but will trap particles of debris with a dimension larger than the distance between the barriers. In other embodiments, the filter barriers 22, 24 may extend less than ½ the distance across the channel, such that the fluid may flow between the barriers but particulate debris may not. Accordingly, in some embodiments, at least one of the plurality of barriers has a rectangular shape, and there is a varying distance between opposing barriers.

The plan view of FIG. 18 shows a plurality of parallel paths 32, 34, 36 and 38 each with filter barriers 24, 26. It should be understood that although the paths 32, 34, 36 and 38 may have the same shape of filter barriers 24, 26 as shown, or they may be different. In some embodiments, the filter barriers may be the same in the parallel paths 32, 34, 36 and 38. In other embodiments, the filter barriers may be different. The paths are shown as being in parallel, but this is also exemplary only, and some filter barrier shapes 32, 34, 36 and 38 may be placed serially before or after other filter barrier shapes. It should be appreciated that since the filter barriers are fabricated lithographically, the shapes may be made arbitrarily complex.

The sample stream may again be input to the filter 2 through an input channel 12, from which it may flow laterally across the face of the substrate 10 as shown by the arrows in. 32-38. The flow may traverse a series of filter barriers 22, 24 in each of the channels 3-38, which are arranged so as not to seal the channel to the flow of the sample stream, but to trap particles of a particular size which may be suspended in the sample stream. In channels 32-38, these filter barriers may be disposed in a staggered arrangement across the width of the channel. However, no barriers extend entirely across the channel so as to seal it against the flow. Instead, the sample stream may flow between the staggered barriers 22 and 24 which may be separated by a distance d. Accordingly, particulate debris with a dimension greater than d may be trapped in the filter barriers 22, 24.

In channels 32-38, the filter barriers may be simple rectangles, similar to filter barriers 22, 24 in FIGS. 17 and 18. In other embodiments, the barriers may have different shapes, such as a tapered shape, narrowing from base to tip, triangular or sawtooth. The filter barriers 34 may lean into or away from the flow. The different shapes and orientations may have different behaviors in terms of effectiveness in trapping particles. Each type of filter shape creates a specific flow circulation around it which traps particles based on their characteristics such as the relative rigidity or stiffness of the particle, or how round or rod-shaped a particle is.

Figure 19:
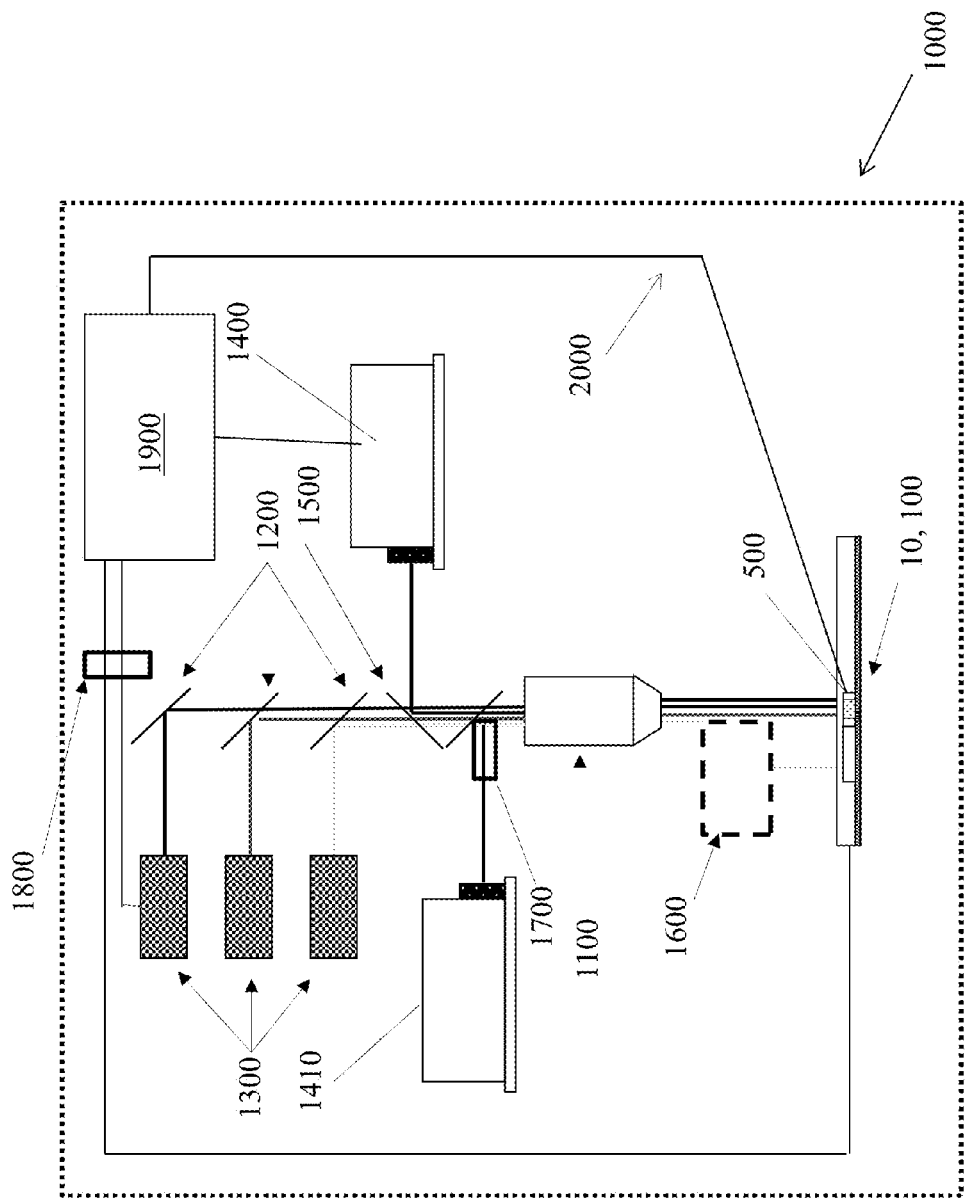
FIG. 19 is a system-level illustration of a microfabricated particle sorting system according to the present invention, showing the placement of the various detection and control components.

The microfabricated particle manipulation device 10 or 100 with focusing element 600 may be used in a particle sorting system 1000 enclosed in a housing containing the components shown in FIG. 19. The MEMS particle manipulation devices 10 or 100 may be enclosed in a plastic, disposable cartridge which is inserted into the system 1000. The insertion area may be a movable stage with mechanisms available for fine positioning of the particle manipulation device 10 or 100 and associated microfluidic channels against one or more data, which orient and position the detection region and particle manipulation device 10 or 100 with respect to the collection optics 1100. If finer positioning is required, the stage may also be a translation stage, which adjusts the positioning based on observation of the location of the movable member 110 relative to a datum.

It should be understood that although FIG. 19 shows a particle sorting system 1000 which uses a plurality of laser sources 1400 and 1410, only a single laser may be required depending on the application. For the plurality of lasers shown in FIG. 19, one of the laser sources 1410 may be used with an associated set of parallel optics (not shown in FIG. 19) to illuminate the at least one additional laser interrogation region. This setup may be somewhat more complicated and expensive to arrange than a single laser system, but may have advantages in that the optical and detection paths may be separated for the different laser interrogation regions. For this embodiment, it may not be necessary to alter the trajectory, spectral content, timing or duration of the laser 1410 light. Although not shown explicitly in FIG. 19, it should be understood that the detection path for additional laser(s) 1410 may also be separate from the detection path for laser 1400. Accordingly, some embodiments of the particle sorting system 1000 may include a plurality of laser sources and a plurality of optical detection paths, whereas other embodiments may only use a single laser source 1400 and collection optics 1100. In the embodiment described here, a plurality of excitation lasers uses a common optical path, and the optical signals are separated electronically by the system shown in FIG. 19.

The embodiment shown in FIG. 19 is based on a FACS-type detection mechanism, wherein one or more lasers 1400, 1410 excites one or more fluorescent tags affixed to the target particles. The laser excitation may take place in multiple interrogation regions. The fluorescence emitted as a result are detected and the signal is fed to a computer 1900. The computer then generates a control signal that controls the electromagnet 500. It should be understood that other detection mechanisms may be used instead, including electrical, mechanical, chemical, or other effects that can distinguish target particles from non-target particles.

Accordingly, the MEMS particle sorting system 1000 shown in FIG. 19 may include a number of elements that may be helpful in implementing the additional interrogation regions. First, an optical manipulating means 1600 may alter the trajectory, spectral content, timing or duration of the laser radiation from laser 1400 to the second or third interrogation spots. Examples of items that may be included in optical manipulating means 1600 are a birefringent crystal, spinning prism, mirror, saturable absorber, acousto-optic modulator, harmonic crystal, Q-switch, for example. More generally, optical manipulating means 1600 may include one or more items that alter laser frequency, amplitude, timing or trajectory along one branch of the optical path to an additional interrogation region.

For example, optical manipulating means 1600 may include a beamsplitter and/or acousto-optic modulator. The beam splitter may separate a portion of the incoming laser beam into a secondary branch or arm, where this secondary branch or arm passes through the modulator which modulates the amplitude of the secondary beam at a high frequency. The modulation frequency may be, for example, about 2 MHz or higher. The light impinging on the first laser interrogation region 101 may, in contrast, be continuous wave (unmodulated). The secondary branch or arm is then directed to the additional laser interrogation region. This excitation will then produce a corresponding fluorescent pattern from an appropriately tagged cell.

This modulated fluorescent pattern may then be picked up by the detection optics 1100, which may recombine the detected fluorescence from other interrogation regions with fluorescence from laser interrogation region 101. The combined radiation may then impinge on the one or more detectors 1300.

An additional optical component 1700 may also alter the frequency, amplitude, timing or trajectory of the second beam path, however, it may perform this operation upstream (on the detector side) of the collection optics 1100 rather than downstream (on the sample side) of it, as does optical component 1600.

The output of detectors 1300 may be analyzed to separate the content corresponding to laser interrogation region 101 from the content corresponding to other laser interrogation regions. This may be accomplished by applying some electronic distinguishing means 1800 to the signals from detectors 1300. The details of electronic distinguishing means 1800 may depend on the choice for optical manipulation means 1600. For example, the distinguishing means 1800 may include a high pass stage and a low pass stage that is consistent with a photoacoustic modulator that was included in optical manipulating means 1600. Alternatively, electronic distinguishing means 1800 may include a filter (high pass and/or low pass) and/or an envelope detector, for example.

Therefore, depending on the choice of optical manipulating means 1600, the unfiltered signal output from detectors 1300 may include a continuous wave, low frequency portion and a modulated, high frequency portion. After filtering through the high pass filter stage, the signal may have substantially only the high frequency portion, and after the low pass stage, only the low frequency portion. These signals may then be easily separated in the logic circuits of computer 1900. Alternatively, the high pass filter may be an envelope detector, which puts out a signal corresponding to the envelop of the amplitudes of the high frequency pulses.

Other sorts of components may be included in electronic distinguishing means 1800 to separate the signals. These components may include, for example, a signal filter, mixer, phase locked loop, multiplexer, trigger, or any other similar device that can separate or distinguish the signals. Component 1800 may also include the high pass and/or low pass electronic filter or the envelope detector described previously. The two sets of signals from the electronic distinguishing means 1800 may be handled differently by the logic circuits 1900 in order to separate the signals.

The description now turns to the fabrication of the devices shown in FIGS. 1-19. Fabrication may begin formation of the valves, 10 or 100. To make these structures, one may begin with formation of the inlaid permeable features 116 and 130 formed in a first substrate. The substrate may be a single crystal silicon substrate, for example. To form these structures, depressions may be formed in these areas of the substrate surface by etching. First, photoresist may be deposited over the substrate surface and removed over the areas corresponding to 116 and 130. Then, the trenches may be formed by, for example, etching the substrate in potassium hydroxide (KOH) to form a suitable depression. A seed layer may be deposited conformally over the first substrate surface and patterned to provide the seed layer for plating NiFe into the trenches. The seed layer may be, for example, Ti/W or Cr/Au and may be deposited by sputtering, CVD or plasma deposition. This layer may be covered with photoresist and patterned according to the desired shape of the areas 116 and 130. Unwanted areas of photoresist and seed layer may then be removed by chemical etching. The permeable features 116 and 10 may then be deposited over the patterned seed layer by sputtering, plasma deposition or electrochemical plating. It is known that permalloy (80% Ni and 20% Fe), for example, can readily be deposited by electroplating.

Alternatively, a liftoff method may be used to deposit a sheet of permeable material, most of which is then lifted off areas other than 116 and 130. Further details into the lithographic formation of inlaid, magnetically permeable materials may be found in, for example, U.S. Pat. No. 7,229,838. U.S. Pat. No. 7,229,838 is hereby incorporated by reference in its entirety. The substrate may then be planarized by chemical mechanical polishing (CMP), leaving a flat surface for the later bonding of a cover plate.

Having made the permeable features 116 and 130, the movable member or valve 110 may be formed. The surface may again be covered with photoresist and patterned to protect the inlaid permeable features 116 and 130. The sample inlet channel 120 and output channels 122 and relieved area 144 may be formed simultaneously with the movable member 110. With movable member 110, and other areas whose topography is to be preserved may be covered with photoresist, the features 110, 120, 122 and 144 may be formed by deep reactive ion etching (DRIE) for example.

To form the fluidic channels, a cover plate may be bonded to the surface of the substrate which was previously planarized for this purpose. The cover plate may be optically transparent to allow laser light to be applied to the particles in the fluid stream flowing in the sample inlet channel 120, and for fluorescence emitted by the fluorescent tags affixed to the particles to be detected by the optical detection system described above. A hole formed in this transparent material may form the waste channel 142. Alternatively, a waste channel 142 may be formed in a second substrate, such as a second silicon substrate, and bonded to the surface of the first substrate. Alternatively, output channel 142 may be formed on the opposite surface of the first substrate using a silicon-on-insulator (SOI) substrate, with waste channel 142 and orifice 140 formed in the handle layer and dielectric layer of the SOI substrate, and the movable feature formed in the device layer.

Additional details for carrying out this process outlined above are well known to those skilled in the art, or readily found in numerous lithographic processing references.

Accordingly, disclosed here is a micromechanical particle manipulation device, formed on a surface of a fabrication substrate. The device may include a microfabricated, movable member formed on the substrate, and having a first diverting surface, wherein the movable member moves from a first position to a second position in response to a force applied to the movable member, wherein the motion is substantially in a plane parallel to the surface of the substrate. It may also include a sample inlet channel formed in the substrate and through which a fluid flows, the fluid including target particles and non-target material, wherein the flow in the sample inlet channel is substantially parallel to the surface. It may also include a plurality of output channels including a sort output channel into which the microfabricated member diverts the target particles, and a waste output channel into which the non-target material flows, and wherein the flow in waste output channel is substantially orthogonal to the plane, and wherein the waste output channel is located directly below at least a portion of the microfabricated member over at least a portion of its motion; and a sheath fluid inlet in fluid communication with the sample inlet channel. Finally, the device may include a focusing element coupled to the sheath fluid inlet and the sample inlet channel, wherein the focusing element is configured to urge the target particles into a particular portion of the sample inlet channel, wherein the focusing element comprises a microfabricated fluid channel with one substantially straight sidewall segment and an adjacent non-parallel sidewall segment, wherein the straight and the non-parallel sidewall segments define a fluid channel segment with a variable channel cross section.

The variable cross section segment of the focusing element channel may define a cavity, wherein the cavity is characterized by a cavity height H, and a cavity width L, and the sample inlet channel is characterized by a sample inlet channel width W and a sample inlet channel depth D. The focusing element may include a plurality of such cavities, and wherein a cavity size is defined as the cavity height H divided by the nominal channel width W, a pitch ratio between the cavities is defined as the distance between the cavities P divided by the height of the cavity H, and an aspect ratio is defined as the nominal width of the channel W divided by the depth of the channel D. These cavities may have cavity size (H/W) of about 5 to 15. The cavities may have a pitch ratio (P/H) of about 4. The flow rate within the focusing element may be about 6 ml/hour. The sample inlet channels may have an aspect ratio W/D of less than about 1.

The focusing element may have at least one acute bend, defining an inner surface of the acute bend and an outer surface of the acute bend, and wherein the plurality of cavities are all disposed on the outside of the acute bend. The straight and non-parallel segments may define expansion/contraction cavities which balance the Dean force and the frictional force, thereby bringing the particles to a stable two-dimensional focus within the focusing element.

The focusing element may be disposed in the same plane as the movable member, and formed in the same substrate.

The sample inlet channel and focusing element may both have characteristic dimensions of about 50 microns. The target particles may be at least one of a stem cell, a cancer cell, a zygote, a protein, a T-cell, a bacteria, a component of blood, and a DNA fragment.

The device may further comprise an electromagnet, and the movable member may move from the first position to the second position when the electromagnet is activated. Accordingly, the force may be at least one of magnetic, electrostatic, and piezoelectric. The device may further comprise a first permeable magnetic material inlaid in the movable member, a first stationary permeable magnetic feature disposed on the substrate, and a first source of magnetic flux external to the movable member and substrate on which the movable member is formed.

The device may be a component of a particle manipulation system. The system may include the micromechanical particle sorting device, at least one laser directed to a laser interrogation region disposed in the sample inlet channel, and at least one set of detection optics that detects a fluorescent signal from a fluorescent tag affixed to the target particle in the fluid. The system may further comprise an electromagnet, and a circuit that provides a control waveform to the electromagnet.

The device may further include a filtering element formed in the same plane as the movable member and the focusing element. The filtering element may be disposed upstream of the movable member and the focusing element.

Also disclosed is a method of making a microfabricated particle manipulation device on a surface of a fabrication substrate. The method may include forming a movable member having a first diverting surface, wherein the movable member is configured to move from a first position to a second position in response to a force applied to the movable member, wherein the motion is substantially in a plane parallel to the surface. The method may further include forming a sample inlet channel formed in the substrate and through which a fluid flows, the fluid including target particles and non-target material, wherein the flow in the sample inlet channel is substantially parallel to the surface. The method may further include forming a plurality of output channels into which the microfabricated member diverts the target particle, and wherein the flow in at least one of the output channels is not parallel to the plane, and wherein at least one output channel is located directly below at least a portion of the microfabricated diverter over at least a portion of its motion. Finally, the method may include forming a sheath fluid inlet in fluid communication with the sample inlet channel, and forming a focusing element coupled to the sheath fluid inlet and the sample inlet channel, wherein the focusing element is configured to urge the target particles into a particular portion of the sample inlet channel, wherein the focusing element is formed in the same substrate as the movable member and sample inlet channel.

In the method, the variable cross section segment of the focusing element channel may defines a cavity, wherein the cavity is characterized by a cavity height H, and a cavity width L, and the sample inlet channel is characterized by a sample inlet channel width W and a sample inlet channel depth D, wherein a cavity size H/W is about 5 to about 15, and an aspect ratio W/D is at least about 1.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A micromechanical particle manipulation device, formed on a surface of a fabrication substrate, comprising:
   a microfabricated, movable member formed on the substrate, and having a first diverting surface, wherein the movable member moves from a first position to a second position in response to a force applied to the movable member, wherein the motion is substantially in a plane parallel to the surface of the substrate;
   a sample inlet channel formed in the substrate and through which a fluid flows, the fluid including target particles and non-target material, wherein the flow in the sample inlet channel is substantially parallel to the surface;
   a plurality of output channels including a sort output channel into which the microfabricated member diverts the target particles, and a waste output channel into which the non-target material flows, and wherein the flow in waste output channel is substantially orthogonal to the plane, and wherein the waste output channel is located directly below at least a portion of the microfabricated member over at least a portion of its motion; and
   a sheath fluid inlet in fluid communication with the sample inlet channel; and
   a focusing element coupled to the sheath fluid inlet and the sample inlet channel, wherein the focusing element is configured to urge the target particles into a particular portion of the sample inlet channel, wherein the focusing element comprises a microfabricated fluid channel with one substantially straight sidewall segment and an adjacent non-parallel sidewall segment, wherein the straight and the non-parallel sidewall segments define a fluid channel segment with a variable channel cross section.

2. The micromechanical particle manipulation device of claim 1, wherein the variable cross section segment of the focusing element channel defines a cavity, wherein the cavity is characterized by a cavity height H, and a cavity width L, and the sample inlet channel is characterized by a sample inlet channel width W and a sample inlet channel depth D.

3. The micromechanical particle manipulation device of claim 2, wherein the focusing element includes a plurality of such cavities, and wherein a cavity size is defined as the cavity height H divided by the nominal channel width W, a pitch ratio between the cavities is defined as the distance between the cavities P divided by the height of the cavity H, and an aspect ratio is defined as the nominal width of the channel W divided by the depth of the channel D.

4. The micromechanical particle manipulation device of claim 3, wherein the cavities have cavity size (H/W) of about 5 to 15.

5. The micromechanical particle manipulation device of claim 3, wherein the cavities have a pitch ratio (P/H) of about 4.

6. The micromechanical particle manipulation device of claim 3, wherein the flow rate within the focusing element is about 6 ml/hour.

7. The micromechanical particle manipulation device of claim 3, wherein the sample inlet channels have an aspect ratio W/D of less than about 1.

8. The micromechanical particle manipulation device of claim 3, wherein the focusing element has at least one acute bend, defining an inner surface of the acute bend and an outer surface of the acute bend, and wherein the plurality of cavities are all disposed on the outside of the acute bend.

9. The micromechanical particle manipulation device of claim 3, wherein the straight and non-parallel segments define expansion/contraction cavities which balance the Dean force and the frictional force, thereby bringing the particles to a stable two-dimensional focus within the focusing element.

10. The micromechanical particle manipulation device of claim 1, wherein the focusing element is disposed in the same plane as the movable member, and formed in the same substrate.

11. The micromechanical particle manipulation device of claim 1, wherein the sample inlet channel and focusing element both have characteristic dimensions of about 50 microns.

12. The micromechanical particle manipulation device of claim 1, wherein the target particles are at least one of a stem cell, a cancer cell, a zygote, a protein, a T-cell, a bacteria, a component of blood, and a DNA fragment.

13. The micromechanical particle manipulation device of claim 1, further comprising:
an electromagnet.

14. The micromechanical particle manipulation device of claim 13, wherein the movable member moves from the first position to the second position when the electromagnet is activated.

15. The micromechanical particle manipulation device of claim 1, further comprising: a first permeable magnetic material inlaid in the movable member;
a first stationary permeable magnetic feature disposed on the substrate; and
a first source of magnetic flux external to the movable member and substrate on which the movable member is formed.

16. The micromechanical particle manipulation device of claim 1, wherein the force is at least one of magnetic, electrostatic, and piezoelectric.

17. A particle manipulation system, comprising:
a microfabricated, movable member formed on the substrate, and having a first diverting surface, wherein the movable member moves from a first position to a second position in response to a force applied to the movable member, wherein the motion is substantially in a plane parallel to the surface of the substrate;
a sample inlet channel formed in the substrate and through which a fluid flows, the fluid including target particles and non-target material, wherein the flow in the sample inlet channel is substantially parallel to the surface;
a plurality of output channels including a sort output channel into which the microfabricated member diverts the target particles, and a waste output channel into which the non-target material flows, and wherein the flow in waste output channel is substantially orthogonal to the plane, and wherein the waste output channel is located directly below at least a portion of the microfabricated member over at least a portion of its motion; and
a sheath fluid inlet in fluid communication with the sample inlet channel; and
a focusing element coupled to the sheath fluid inlet and the sample inlet channel, wherein the focusing element is configured to urge the target particles into a particular portion of the sample inlet channel, wherein the focusing element comprises a microfabricated fluid channel with one substantially straight sidewall segment and an adjacent non-parallel sidewall segment, wherein the straight and the non-parallel sidewall segments define a fluid channel segment with a variable channel cross section;
at least one laser directed to a laser interrogation region disposed in the sample inlet channel; and
at least one set of detection optics that detects a fluorescent signal from a fluorescent tag affixed to the target particle in the fluid.

18. The particle manipulation system of claim 14, further comprising:
an electromagnet; and
a circuit that provides a control waveform to the electromagnet.

19. A method of making a microfabricated particle manipulation device on a surface of a fabrication substrate, comprising:
forming a movable member having a first diverting surface, wherein the movable member is configured to move from a first position to a second position in response to a force applied to the movable member, wherein the motion is substantially in a plane parallel to the surface;
forming a sample inlet channel formed in the substrate and through which a fluid flows, the fluid including target particles and non-target material, wherein the flow in the sample inlet channel is substantially parallel to the surface;
forming a plurality of output channels into which the microfabricated member diverts the target particle, and wherein the flow in at least one of the output channels is not parallel to the plane, and wherein at least one output channel is located directly below at least a portion of the microfabricated diverter over at least a portion of its motion;
forming a sheath fluid inlet in fluid communication with the sample inlet channel; and
forming a focusing element coupled to the sheath fluid inlet and the sample inlet channel, wherein the focusing element is configured to urge the target particles into a particular portion of the sample inlet channel, wherein the focusing element is formed in the same substrate as the movable member and sample inlet channel.

20. The method of making the microfabricated particle manipulation device of claim 19, wherein the variable cross section segment of the focusing element channel defines a cavity, wherein the cavity is characterized by a cavity height H, and a cavity width L, and the sample inlet channel is characterized by a sample inlet channel width W and a sample inlet channel depth D, wherein a cavity size H/W is about 5 to about 15, and an aspect ratio W/D is at least about 1.

21. The micromechanical particle manipulation device of claim 10, further comprising:
a filtering element formed in the same plane as the movable member and the focusing element.

22. The micromechanical particle manipulation device of claim 21, wherein the filtering element is disposed upstream of the movable member and the focusing element.

* * * * *